US011891615B2

(12) United States Patent
Humble

(10) Patent No.: US 11,891,615 B2
(45) Date of Patent: Feb. 6, 2024

(54) PROCESS TO PRODUCE KLOTHO PROTEIN IN VITRO

(71) Applicant: Gail Marion Humble, Napa, CA (US)

(72) Inventor: Gail Marion Humble, Napa, CA (US)

(*) Notice: Subject to any disclaimer, the term of this patent is extended or adjusted under 35 U.S.C. 154(b) by 140 days.

(21) Appl. No.: 17/301,637

(22) Filed: Apr. 9, 2021

(65) Prior Publication Data

US 2021/0388380 A1 Dec. 16, 2021

Related U.S. Application Data

(60) Provisional application No. 62/705,083, filed on Jun. 10, 2020.

(51) Int. Cl.
| | | |
|---|---|---|
| *C12N 15/85* | (2006.01) | |
| *C12N 5/077* | (2010.01) | |
| *A61K 8/98* | (2006.01) | |

(52) U.S. Cl.
CPC ............... *C12N 15/85* (2013.01); *A61K 8/98* (2013.01); *C12N 5/0656* (2013.01); *C12N 5/0669* (2013.01); *C12N 2501/105* (2013.01); *C12N 2501/11* (2013.01); *C12N 2501/115* (2013.01); *C12N 2501/135* (2013.01); *C12N 2501/15* (2013.01); *C12N 2501/165* (2013.01); *C12Y 302/01031* (2013.01)

(58) Field of Classification Search
CPC ....... C12N 15/85; C12N 5/0675; A61K 35/28
See application file for complete search history.

(56) References Cited

U.S. PATENT DOCUMENTS

| | | |
|---|---|---|
| 6,265,180 B1 | 7/2001 | Zuelli et al. |
| 6,558,941 B2 | 5/2003 | Zuelli et al. |
| 6,579,850 B1 | 6/2003 | Nabeshima et al. |
| 6,986,903 B2 | 1/2006 | Zulli et al. |
| 7,537,903 B2 | 5/2009 | Kuro-o et al. |
| 8,206,721 B2 | 6/2012 | Stutz et al. |
| 8,481,031 B2 | 7/2013 | Glass et al. |
| 9,738,716 B2 | 8/2017 | Mondal et al. |
| 9,925,137 B2 | 3/2018 | Stout et al. |
| 10,004,680 B2 | 6/2018 | Florence et al. |
| 10,016,565 B2 | 7/2018 | Adams et al. |
| 2010/0316720 A1 | 12/2010 | Stutz et al. |
| 2013/0287714 A1 | 10/2013 | Gohla et al. |
| 2015/0050316 A1 | 2/2015 | Stangl et al. |
| 2018/0037868 A1* | 2/2018 | Günther ................. A61K 48/00 |
| 2018/0110721 A1 | 4/2018 | Bell et al. |

FOREIGN PATENT DOCUMENTS

| | | |
|---|---|---|
| CN | 104940121 A | 9/2015 |
| WO | 2017210607 A1 | 12/2017 |
| WO | 2018001570 A1 | 1/2018 |
| WO | 2018098375 A1 | 5/2018 |

OTHER PUBLICATIONS

Pittenger et al. "Mesenchymal Stem Cells from Adult Bone Marrow" in Mesenchymal Stem Cells. pp. 30-31. Totowa: Humana Press. 2008. (Year: 2008).*
Van Loon et al. Shedding of Klotho by ADAMs in the kidney. American Journal of Physiology-Renal Physiology 2015, 309:359-368. (Year: 2015).*
Lee et al. Establishment of transgenic porcine fibroblasts expressing a human klotho gene and its effects on gene expression and preimplantation development of cloned embryos. DNA and Cell Biology 2017, 36;1:42-49. (Year: 2017).*
Markiewicz et al. Role of Klotho in migration and proliferation of human dermal microvascular endothelial cells. Microvascular Research 2016, 107:76-82. (Year: 2016).*
Sun et al. Overexpression of Klotho suppresses liver cancer progression and induces cell apoptosis by negatively regulating wnt/β signaling pathway. World Journal of Surgical Oncology 2015, 13:307. (Year: 2015).*
Bruggisser et al. Cell-specific targeting by Clostridium perfringens β-toxin unraveled: the role of CD31 as the toxin receptor. bioRxiv 2019, 787242; doi: https://doi.org/10.1101/787242. (Year: 2019).*
Christensen et al., "The quest for genetic determinants of human longevity: challenges and insights"; pp. 1-27; Nat Rev Genet. Jun. 2006 ; 7(6): 436-448.
Dubal DB, et al. "Life extension factor klotho enhances cognition." Cell Rep. May 22, 2014;7(4):1065-76.
Dubal DB, et al. "Life extension factor klotho prevents mortality and enhances cognition in hAPP transgenic mice." J Neurosci. Feb. 11, 2015;35(6):2358-71.
Drueke et al. "Klotho spins the thread of life—what does Klotho do to the receptors of fibroblast growth factor-23 (FGF23)?" ; Nephrol Dial Transplant (2007) 22: 1524-1526.
"Isolation, Primary culture and cryopreservation of human neonatal fibroblasts." Fibroblast Protocols (2018) pp. 1-5, ThermoFisher Scientific Online Library.
Hui, et al., "Klotho suppresses the inflammatory responses and ameliorates cardiac dysfunction in aging endotoxemic mice", Oncotarget, 2017; pp. 15663-15676; vol. 8, No. 9.

(Continued)

*Primary Examiner* — Allison M Fox
*Assistant Examiner* — Jennifer S Spence
(74) *Attorney, Agent, or Firm* — Dunlap Bennett & Ludwig, PLLC; Anna L. Kinney

(57) ABSTRACT

A method of producing Klotho protein includes preparing a Klotho plasmid DNA vector, culturing cells, transfecting the cells with the Klotho plasmid DNA vector in a cell culture medium, growing the transfected cells, and harvesting the cell culture supernatant by removing the transfected cells. The Klotho plasmid DNA vector has a mammalian selection marker and a Klotho open reading frame. The cells are primary fibroblast cells and/or mesenchymal stromal cells. A method of manufacturing a cosmetic composition includes combining Klotho protein or the cell culture supernatant with a cosmetically acceptable vehicle. A method of treating a patient to improve the condition and appearance of aging skin includes topically administering the cosmetic composition to the patient. By upregulating the Klotho gene in vitro and incorporating the Klotho protein and growth factors into a composition, transepidermal water loss, skin atrophy, and free radical damage to the skin may be addressed.

16 Claims, 12 Drawing Sheets

Specification includes a Sequence Listing.

(56) References Cited

OTHER PUBLICATIONS

Jumble G, et al. "Discovery of aging gene leads to formulation of the most effective anti-aging cosmeceutical: Klotho Skin", 2018, pp. 1-5.

Humble G, et al. "Proliferative and pleiotropic effects of supplementing snow algae species, *Chlamydomonas nivalis*, in culturing human fibroblast conditioned media", 2018, pp. 1-7.

Ito S, et al. "Impaired negative feedback suppression of bile acid synthesis in mice lacking betaKlotho", J. Clin. Invest. Aug. 2005; 115(8):2202-2208.

Ito S, et al. "Molecular cloning and expression analyses of mouse betaklotho, which encodes a novel Klotho family protein". Mech Dev. Nov. 2000; 98(1-2):115-119.

Kuro-O, M. "Klotho and aging", Biochim. Biophys. Acta., 2009, pp. 1049-1058, vol. 1790, No. 10.

Kurosu H, et al. "Suppression of aging in mice by the hormone Klotho". Science. Sep. 16, 2005;309(5742):1829-33.

Kurosu H, et al., "Regulation of Fibroblast Growth Factor-23 Signaling by Klotho", J. Biol. Chem., 2006, pp. 6120-6123, vol. 281, No. 10.

Li D, et al. "Enhanced Expression of Secreted α-Klotho in the Hippocampus Alters Nesting Behavior and Memory Formation in Mice". Front. Cell Neurosci. Apr. 2, 2019;13:133, pp. 1-16.

Lim K, et al., "Vascular Klotho Deficiency Potentiates the Development of Human Artery Calcification and Mediates Resistance to Fibroblast Growth Factor 23". 2012; Circulation. 125:2243-2255.

Manolis, AS. "Klotho, spinning the thread of life: an anti-ageing gene". Hospital Chronicles 2012, 7: 129-32.

Medici, et al., "FGF-23—Klotho signaling stimulates proliferation and prevents vitamin D—induced apoptosis", J. Cell Biol., 2008, pp. 459-465, vol. 182, No. 3.

Nagai T, et al. "Cognition impairment in the genetic model of aging klotho gene mutant mice: a role of oxidative stress." FASEB J. Jan. 2003;17(1):50-72.

Remias et al.; "Ecophysiology, secondary pigments and ultrastructure of *Chlainomonas* sp. (Chlorophyta) from the European Alps compared with Chlamydomonas nivalis forming red snow"; FEMS Microbiology Ecology, 92, No. 4, 2016.

Salminen A, et al. "AMP-activated protein kinase (AMPK) controls the aging process via an integrated signaling network". Ageing Research Reviews 2012; 11: 230-241.

Schmid et al., "Rejuvenating effect of snow algae analysed"; Personal Care, Apr. 2014; pp. 31-34.

Skjanes et al.; "Potential for green microalgae to produce hydrogen, pharmaceuticals and other high value products In a combined process"; Critical Reviews in Biotechnology, 2013; 33(2): 172-215.

"Snow Algae Powder. Key to skin's longevity", Mibelle® Biochemistry.

"Snow Algae Powder—The Mystery of Red Snow"; Cosmetics; preview; Feb. 2014; Mibelle Group Biochemistry.

Takashima A. "Establishment of Fibroblast Cultures" Current Protocols in Cell Biology. Preparation and isolation of cells (1998) pp. 2.1.1-2.1.12.

"The secret of the snow algae"; The global information on cosmetics & fragrances Guide of cosmetic ingredients; 2014; pp. 157-161.

Yamamoto et al. "Regulation of Oxidative Stress by the Anti-aging Hormone Klotho", J. Biol. Chem. (2005) 280(45):38029-38034.

Zhang et al., "Sex-Based Differences in Gut Microbiota Composition in Response to Tuna Oil and Algae Oil Supplementation in a D-galactose-Induced Aging Mouse Model"; Frontiers in Aging Neuroscience (2018); 10:187, pp. 1-12.

\* cited by examiner

FIG. 1

| ORIGIN 1 | mpasapprrp | rppppslsll | lvllgiggrr | lra epgdgaq | twarfsrppa | peaagffqgt |
|---|---|---|---|---|---|---|
| 61 | fpdgflwavg | saayqteggw | qqhgkgasiw | dtfthhplap | pgdsrnaslp | lgapsplqpa |
| 121 | tgdvasdsyn | nvfrdtealr | elgvthyrfs | iswarvlpng | sagvpnregl | ryyrrllerl |
| 181 | relgvqpvvt | lyhwdlpqrl | qdayggwanr | aladhfrdya | eicfrhfggq | vkywitidnp |
| 241 | yvvawhgyat | grlapgirgs | prlgylvahn | lllahakvwh | lyntsfrptq | ggqvsialss |
| 301 | hwinprrmtd | hsikecqksl | dfvlgwfakp | vfldgdtypes | mknnlssllp | dftesekkfi |
| 361 | kgtadffalc | fgptlsfqjl | dphmkfrqje | spnlrqllsw | idlefnhpqi | fivengwfvs |
| 421 | gttkrddaky | myylkkfime | tlkaikldgv | dvlgytawsl | mdgfewhrgy | sirrgifyvd |
| 481 | flscdkmllp | kssalfyqkl | iekngfpplp | enqplegtfp | cdfawgvvdn | yiqvdttlsq |
| 541 | ftdlnvylwd | vhhskrllkv | dgvvtkkrks | ycvdfraaiqp | qialtqemhv | thfrfsldwa |
| 601 | lilplgnqsq | vnhtilqyyr | cmaselvrvn | itpvvalwqp | mapnqglprl | larqgawenp |
| 661 | ytalafaeya | rlcfqelghh | vklwitmnep | ytrnmtysag | hnllkahala | whvynekfrh |
| 721 | aqngkisial | qadwiepacp | fscqkdkevae | rvlefdigwl | aepifgsgdy | pwvmrdwlnq |
| 781 | rnnfllpyft | edekkliqgt | fdflalshyt | tilvdseked | pikyndylev | qemtditwin |
| 841 | spsqvavvpw | glrkvlnwlk | fkygdlpmyi | isngiddglh | aeddqlrvyy | mqnyinealk |
| 901 | ahildginlc | gyfaysfndr | taprfglyry | aadqfepkas | mkhyrkiids | ngfpgpetle |
| 961 | rfcpeeftvc | tecsffhtrk | sl llaflaflf | faslslsli | fvlyskkgrrs | yk |

FIG.2

```
TTTTGTAATACGACTCACTATAGGGCGGCCGCCCCGCGGAATTGTCGACTGGATCGGTACCGAGGAGATCTGCCGCC|GCGATCGC|C
ATGGCCCAGCGCCAGCCCCGCGCCGCCCCCGGCGCCGCCGCCGCCCGCCTGGGCGGGAAGACCCGCTGCTGTCTCTGCCCCCCGAGCCGCGGCCTCTTGGGGCCTCTTCCAGGGCA
CCTGCGGTGCGGAGCGGGCGACGGCGTCGGGGCCGGGCGCAGACCTGGGCCAGGCAGGCAGGGGCTGGCAGCAGGGCGCCAGTCGCCGTTGGGCGCTGCGCCGTGCGCCGTCCATCT
CCTTCCCGACGGTTCACCCACCACCACCCCTGGCACCCCTACCAGCGCGCCGCCGGGAGACTCCCGGAGACCTCTTCCGGACACGACCAGGGAACGCCAGTCTGCGGTGCGCTGTCG
GGGATACGTTCACCCACCACCACCCCTGGCACCCCTACCAGCGCGCCGCCGGGAGACTCCCGGAGACCTCTTCCGGACACGACCAGGGAACGCCAGTCTGCGGTCGCCGTCAGCCCG
CCACCGTCGTGGGCGCGGGCGGCGCAGCCGAGTGTCCCAATGGCGCGGGCGGGACGCGGGCGTCCCAACTGGGTGTCAGCCCGGGTCACCGTCACTGCGGTTCACCCGGCTCACTACGCTTCT
CCATCTCGGGGAGCTGGCAGCCCTGGCCGACCACTTCAGGGATTACGCGGAGCTCGTGCTCCACACTGCTCCTTCCGCCACTTGGCATCGGCCTCGCCCTGCCCGGCATCCTCCCTGAGTCCGCCGTACCTGGTGCGCA
CGGCGCCTGGCCTGGCGACCACTTCAGGGATTACGCGGAGCTCGTGCTCCACACTGCTCCTTCCGCCACTTGGCATCGGCCTCGCCCTGCCCGGCATCCTCCCTGAGTCCGCCGTACCTGGTGCGCA
CCCTACGTGGTGGCTGGCACGGCATCGCCACCGGGCATCTGGCATCCTGGCATCTCTACAATACTCTTTCCGTCCCACTCAGGGAGGTCAGGTGTCCATTGTACTAGGTTGGTTTGCCAAACCCG
CAACCTCCTCCTGGCTCATGCCAAAGTCTGGACTTGCTTGCTTTTGCCAAGAATGACCGACGACCAGCAGCATCCACACAGCAGATCAAAAGAATGTCAAAAACCTTCAGCTTCAGCTTCGACACCGTCACCGTCACTAGTGGTTGCCAAACCCG
TCACTGGATCAATCTCGAAGAATGACCGACGACCAGCAGCATCCACACAGCAGATCAAAAGAATGTCAAAAACCTTCAGCTTCAGCTTCGACACCGTCACCGTCACTAGTGGTTGCCAAACCCG
TATTTATTGATGGTGACTATCCCGAGAGCATGAAGAGCATGAAGAGAATGCGAGAGCATGAAGAGAATGCGAGACCCTTGAGTCGATGCCACCCCAATGGCGCCCAATTCATCAAAG
GAACTGCTGACTGTTTTGCTCTTCCCTGGATTGACCTTGAACCTTGAACCTTGAACATCTCAAATATTTATTGTGGAAAATGGCTGGTTTGTCTCAGGGACCACCAA
CCTGAGGCAACTGCTTTGCTCTTCCTGGATTGACCTTGAACCTTGAACATCTCAAATATTTATTGTGGAAAATGGCTGGTTTGTCTCAGGGACCACCAA
GAGAGATGATGCCAAATATATGTTCATTCACTCCAAAAAAGTTCATCATGGAAAACCTTAAAAGCCATCAAGCTGGATGGGGTGGATGATGCTCATCGGG
TATACCGATGGTCCCATGGTCTTCAAGGATGCGGACACAGAGAAGTTACAGCCATCAGGCGTCAGCACTACTCAGAGCGTATACAAGGAATATGACATACAGTG
CAAGATGTTGTTGCCAAATGCCATGGTCCCATGGTCTTCAAGGATGCGGACACAGAGAAGTTACAGCCATCAGGCGTCAGCACTACTCAGAGCGTATACAAGGAATATGACATACAGTG
AAGGGACATTTCCCTGTCACTTGCTTGGGGAGTTGTTGACAACTACATTCAAGTAGATACACTTCAAGGAAAATCAAGTAGACATTCAAGTAGATACACTTCAAGGAAAATCAAGTAGATACACTTCAAGGAAAATCAAGTAG
ACCTGTGGATGTCACACAGTTTACTCCAGGAACCATCGTCAGATACCTGGAAAAGTAATCCTAGAAGGCTTATTAAGTGATGGGGTATTTATAAAGGCAAATGCAGTTACTGCAGCCA
CATCCAGCCCAGTGAACTTACTCCAGGAACCATCGTCAGATACCTGGAAAAGTAATCCTAGAAGGCTTATTAAGTGATGGGGTATTTATAAAGGCAAATGCAGTTACTGCAGCCA
GTCCAGGTCATGGCCCGAACCAAGGACTGCCGGCCATCAGCTGGCCCTCTGGCAGTCAAGTTTGGATAACGATGAATGGAAAAGTTTAGGCATGCCGAGATGCTCAGAGTTTGACATTGGCTGG
CAGCCTATGCCCGACTGTGTCTTCAAGAGGCCCATGGCCCATGGTCCTCGGCTTGCATGTGTACAATGGACAAAGAGAGTGGCGAACCAAGAGTTTGGATAACGATGAATGGAAAAGTTTAGGCATGCCGAGATGCTCAGAGTTTGACATTGGCTGG
CTTGCAGGGCTGATAGAACCTTCGAAGGCCACAGACCGCACAGCAATGGTTTCCCGGCCCAAAGAAAAGGACTGGCGAACCAAAGAGAGTGGCTGAACAAGAGACAATTTCTTCTTCCTATTTCACT
CTGGCTGAGCAATTTCGGCTCTGGAAGATTATCCATGGGTGATGAGGGTACCTTTGGCTTTAAGCATCACGTGGCTGACTCTTTAAGCAATCGGCAAGGAATAAACCAATAAGACTTCAGAAAAAGAAGATCC
GAAGATGAAAAATACAATGATTACTAGAAGGCTGAAGTGCAAACGCTAAGAAAAATCAAGAGAGGCCATGGCTAGTCAGAGTCAGAGTTAAAGACTCAGAAAAAGAAGATCC
AATAAAATACAAATGATTACTAGAAGGCTGAAGTGCAAACGCTAAGAAAAATCAAGAGAGGCCATGGCTAGTCAGAGTCAGAGTTAAAGACTCAGAAAAAGAAGATCC
GTTGCGCAAAGTCTGAACTGGCTGAAGTTCAAGTACGGAGTGCTGAAGTTCAAGTACGGAGTGGGCAGAGAGAGTGGCTAACAGAGGGCTGCATGCTGCATGCT
GAGGACGACCAGCAGTGAGGGTTAACGGCACAGCGCACAGCGACCAAGGTCAAGTTCAAGTTCAGATGGGCATATCAATCTTTGCGGAT
ACTTTGCTTATTCGTTAACGACCGCACAGTGGTTTCCGGGCCCAGAGATTTGTCAGAAGATTTCTCATGCTCAAGGCATCCATGAAACCATGAAC
ATTACAGGAAATTATTGACAGCAATGGTTTTCGGGCCCAGAGATTTGTCAGAAGATTTCTCATGCTCAAGGCATCCATGAAACCGTGTACTGAGTGC
AGTTTTTTCACACCGAAAATTAGACGCAAGTCTTTACGCGCTTTCATAGCTTTCATAGCTTTGCTCATTTTGCTTCTCTCTCTCATATTTCTATTTTACTACTCGAAGA
AAGGCAGAAGGAAGTTTACAAA
ACGCGT|AGGGGCCGCGTGAGCAGAAACTCATCTCAGAAGAGGATCTGGCAGCAAATGATATCCTGGAACAGAAGATGAGAAGATGAGAAGGATAAGG|TTTAA
```

FIG.3

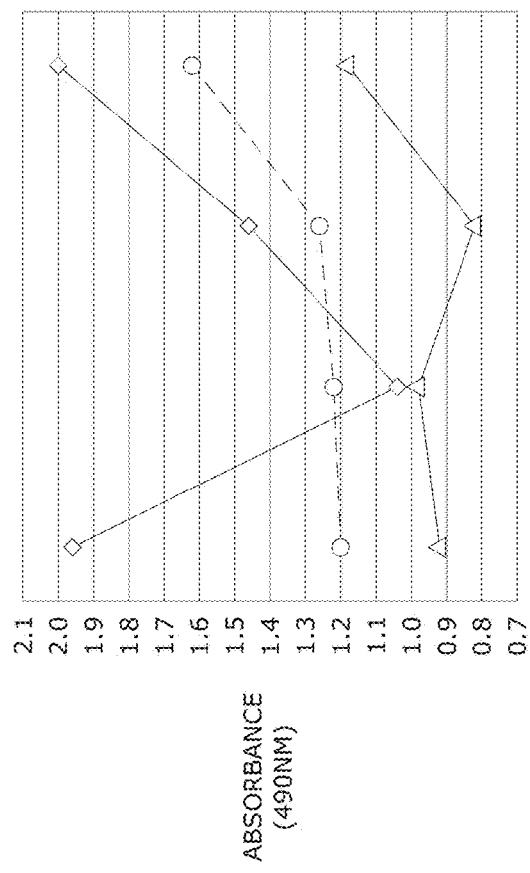
FIG. 8A
FIG. 8B

SEQUENCE LISTING

```
<160> NUMBER OF SEQ ID NOS: 3

<210> SEQ ID NO 1
<211> LENGTH: 1012
<212> TYPE: PRT
<213> ORGANISM: Homo sapiens

<400> SEQUENCE: 1

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175
```

```
Leu Glu Arg Leu Arg Glu Leu Gly Val Gln Pro Val Thr Leu Tyr
            180                 185                 190

His Trp Asp Leu Pro Gln Arg Leu Gln Asp Ala Tyr Gly Gly Trp Ala
            195                 200                 205

Asn Arg Ala Leu Ala Asp His Phe Arg Asp Tyr Ala Glu Leu Cys Phe
210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
            275                 280                 285

Thr Gln Gly Gly Gln Val Ser Ile Ala Leu Ser Ser His Trp Ile Asn
            290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
            355                 360                 365

Leu Cys Phe Gly Pro Thr Leu Ser Phe Gln Leu Leu Asp Pro His Met
370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
            435                 440                 445

Gly Val Asp Val Ile Gly Tyr Thr Ala Trp Ser Leu Met Asp Gly Phe
450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
            515                 520                 525

Asp Asn Tyr Ile Gln Val Asp Thr Thr Leu Ser Gln Phe Thr Asp Leu
            530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
            580                 585                 590
```

```
Phe Arg Phe Ser Leu Asp Trp Ala Leu Ile Leu Pro Leu Gly Asn Gln
            595                 600                 605

Ser Gln Val Asn His Thr Ile Leu Gln Tyr Tyr Arg Cys Met Ala Ser
610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
            645                 650                 655

Trp Glu Asn Pro Tyr Thr Ala Leu Ala Phe Ala Glu Tyr Ala Arg Leu
                660                 665                 670

Cys Phe Gln Glu Leu Gly His His Val Lys Leu Trp Ile Thr Met Asn
        675                 680                 685

Glu Pro Tyr Thr Arg Asn Met Thr Tyr Ser Ala Gly His Asn Leu Leu
    690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
        755                 760                 765

Asp Tyr Pro Trp Val Met Arg Asp Trp Leu Asn Gln Arg Asn Asn Phe
    770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
            820                 825                 830

Met Thr Asp Ile Thr Trp Leu Asn Ser Pro Ser Gln Val Ala Val Val
        835                 840                 845

Pro Trp Gly Leu Arg Lys Val Leu Asn Trp Leu Lys Phe Lys Tyr Gly
    850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
    930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Leu Ala Phe Ile Ala Phe Leu Phe Phe Ala
            980                 985                 990

Ser Ile Ile Ser Leu Ser Leu Ile Phe Tyr Tyr Ser Lys Lys Gly Arg
        995                 1000                1005

Arg Ser Tyr Lys
```

1010

<210> SEQ ID NO 2
<211> LENGTH: 5003
<212> TYPE: DNA
<213> ORGANISM: Homo sapiens

<400> SEQUENCE: 2

| | | | | | |
|---|---|---|---|---|---|
| cgcgcagcat | gcccgccagc | gccccgccgc | gccgcccgcg | gccgccgccg | ccgtcgctgt | 60 |
| cgctgctgct | ggtgctgctg | ggcctgggcg | gccgccgcct | gcgtgcggag | ccgggcgacg | 120 |
| gcgcgcagac | ctgggcccgt | ttctcgcggc | ctcctgcccc | cgaggccgcg | ggcctcttcc | 180 |
| agggcacctt | ccccgacggc | ttcctctggg | ccgtgggcag | cgccgcctac | cagaccgagg | 240 |
| gcggctggca | gcagcacggc | aagggtgcgt | ccatctggga | tacgttcacc | caccaccccc | 300 |
| tggcaccccc | gggagactcc | cggaacgcca | gtctgccgtt | gggcgccccg | tcgccgctgc | 360 |
| agcccgccac | cggggacgta | gccagcgaca | gctacaacaa | cgtcttccgc | gacacggagg | 420 |
| cgctgcgcga | gctcggggtc | actcactacc | gcttctccat | ctcgtgggcg | cgagtgctcc | 480 |
| ccaatggcag | cgcgggcgtc | cccaaccgcg | aggggctgcg | ctactaccgg | cgcctgctgg | 540 |
| agcggctgcg | ggagctgggc | gtgcagcccg | tggtcaccct | gtaccactgg | gacctgcccc | 600 |
| agcgcctgca | ggacgcctac | ggcggctggg | ccaaccgcgc | cctggccgac | cacttcaggg | 660 |
| attacgcgga | gctctgcttc | cgccacttcg | gcggtcaggt | caagtactgg | atcaccatcg | 720 |
| acaacccta | cgtggtggcc | tggcacggct | acgccaccgg | gcgcctggcc | ccggcatcc | 780 |
| ggggcagccc | gcggctcggg | tacctggtgg | cgcacaacct | cctcctggct | catgccaaag | 840 |
| tctggcatct | ctacaatact | tctttccgtc | ccactcaggg | aggtcaggtg | tccattgccc | 900 |
| taagctctca | ctggatcaat | cctcgaagaa | tgaccgacca | cagcatcaaa | gaatgtcaaa | 960 |
| aatctctgga | ctttgtacta | ggttggtttg | ccaaacccgt | atttattgat | ggtgactatc | 1020 |
| ccgagagcat | gaagaataac | ctttcatcta | ttctgcctga | ttttactgaa | tctgagaaaa | 1080 |
| agttcatcaa | aggaactgct | gactttttg | ctctttgctt | tggacccacc | ttgagttttc | 1140 |
| aacttttgga | ccctcacatg | aagttccgcc | aattggaatc | tcccaacctg | aggcaactgc | 1200 |
| tttcctggat | tgaccttgaa | tttaaccatc | ctcaaatatt | tattgtggaa | aatggctggt | 1260 |
| tgtctcagg | gaccaccaag | agagatgatg | ccaaatatat | gtattacctc | aaaaagttca | 1320 |
| tcatggaaac | cttaaaagcc | atcaagctgg | atggggtgga | tgtcatcggg | tataccgcat | 1380 |
| ggtccctcat | ggatggtttc | gagtggcaca | gaggttacag | catcaggcgt | ggactcttct | 1440 |
| atgttgactt | tctaagccag | gacaagatgt | tgttgccaaa | gtcttcagcc | ttgttctacc | 1500 |
| aaaagctgat | agagaaaaat | ggcttccctc | ctttacctga | aaatcagccc | ctagaaggga | 1560 |
| catttccctg | tgactttgct | tggggagttg | ttgacaacta | cattcaagta | gataccactc | 1620 |
| tgtctcagtt | taccgacctg | aatgtttacc | tgtgggatgt | ccaccacagt | aaaaggctta | 1680 |
| ttaaagtgga | tggggttgtg | accaagaaga | ggaaatccta | ctgtgttgac | tttgctgcca | 1740 |
| tccagcccca | gatcgcttta | ctccaggaaa | tgcacgttac | acattttcgc | ttctccctgg | 1800 |
| actgggcct | gattctccct | ctgggtaacc | agtcccaggt | gaaccacacc | atcctgcagt | 1860 |
| actatcgctg | catggccagc | gagcttgtcc | gtgtcaacat | caccccagtg | gtggccctgt | 1920 |
| ggcagcctat | ggccccgaac | caaggactgc | cgcgcctcct | ggccaggcag | ggcgcctggg | 1980 |
| agaaccccta | cactgccctg | gcctttgcag | agtatgcccg | actgtgcttt | caagagctcg | 2040 |
| gccatcacgt | caagctttgg | ataacgatga | atgagccgta | tacaaggaat | atgacataca | 2100 |

```
gtgctggcca caaccttctg aaggcccatg ccctggcttg gcatgtgtac aatgaaaagt    2160
ttaggcatgc tcagaatggg aaaatatcca tagccttgca ggctgattgg atagaacctg    2220
cctgcccttt ctcccaaaag gacaaagagg tggccgagag agttttggaa tttgacattg    2280
gctggctggc tgagcccatt ttcggctctg gagattatcc atgggtgatg agggactggc    2340
tgaaccaaag aaacaatttt cttcttcctt atttcactga agatgaaaaa aagctaatcc    2400
agggtacctt tgacttttg gctttaagcc attataccac catccttgta gactcagaaa     2460
aagaagatcc aataaaatac aatgattacc tagaagtgca agaaatgacc gacatcacgt    2520
ggctcaactc ccccagtcag gtggcggtag tgccctgggg gttgcgcaaa gtgctgaact    2580
ggctgaagtt caagtacgga gacctcccca tgtacataat atccaacgga atcgatgacg    2640
ggctgcatgc tgaggacgac cagctgaggg tgtattatat gcagaattac ataaacgaag    2700
ctctcaaagc ccacatactg gatggtatca atctttgcgg atactttgct tattcgttta    2760
acgaccgcac agctccgagg tttggcctct atcgttatgc tgcagatcag tttgagccca    2820
aggcatccat gaaacattac aggaaaatta ttgacagcaa tggtttcccg ggcccagaaa    2880
ctctggaaag attttgtcca gaagaattca ccgtgtgtac tgagtgcagt ttttttcaca    2940
cccgaaagtc tttactggct ttcatagctt ttctattttt tgcttctatt atttctctct    3000
cccttatatt ttactactcg aagaaaggca gaagaagtta caaatagttc tgaacatttt    3060
tctattcatt cattttgaaa taattatgca gacacatcag ctgttaacca tttgcacctc    3120
taagtgttgt gaaactgtaa atttcataca tttgacttct agaaaacatt tttgtggctt    3180
atgacagagg ttttgaaatg ggcataggtg atcgtaaaat attgaataat gcgaatagtg    3240
cctgaatttg ttctctttt gggtgattaa aaaactgaca ggcactataa tttctgtaac     3300
acactaacaa aagcatgaaa aataggaacc acaccaatgc aacatttgtg cagaaatttg    3360
aatgacaaga ttaggaatat tttcttctgc acccacttct aaatttaatg ttttttctgga   3420 agtagtaatt gcaagagttc gaatagaaag ttatgtacca agtaaccatt tctcagctgc    3480
cataataatg cctagtggct tcccctctgt caaatctagt ttcctatgga aaagaagatg    3540
gcagatacag gagagacgac agagggtcct aggctggaat gttcctttcg aaagcaatgc    3600
ttctatcaaa tactagtatt aatttatgta tctggttaat gacatacttg gagagcaaat    3660
tatgaaaatg tgtattttat atgattttg aggtcctgtc taaaccctgt gtccctgagg     3720
gatctgtctc actggcatct tgttgagggc cttgcacata ggaaactttt gataagtatc    3780
tgcgaaaaaa caaacatgaa tcctgtgata ttgggctctt caggaagcat aaagcaattg    3840
tgaaatacag tataccgcag tggctctagg tggaggaaag gaggaaaaag tgcttattat    3900
gtgcaacatt atgattaatc tgattataca ccattttga gcagatcttg gaatgaatga     3960
catgaccttt ccctagagaa taaggatgaa ataatcactc attctatgaa cagtgacact    4020
actttctatt cttagctgt actgtaattt cttgagttg atagttttac aaattcttaa      4080
taggttcaaa agcaatctgg tctgaataac actggatttg tttctgtgat ctctgaggtc    4140 tatttatgt ttttgctgct acttctgtgg aagtagcttt gaactagttt tactttgaac     4200
tttcacgctg aaacatgcta gtgatatcta gaaagggcta attaggtctc atcctttaat    4260
gccccttaaa taagtcttgc tgattttcag acagggaagt ctctctatta cactggagct    4320
gttttataga taagtcaata ttgtatcagg caagataaac caatgtcata acaggcattg    4380
ccaacctcac tgacacaggg tcatagtgta taataatata ctgtactata taatatatca    4440
```

```
tctttagagg tatgattttt tcatgaaaga taagcttttg gtaatattca ttttaaagtg      4500
gacttattaa aattggatgc tagagaatca agtttatttt atgtatatat ttttctgatt      4560
ataagagtaa tatatgttca ttgtaaaaat ttttaaaaca cagaaactat atgcaaagaa      4620
aaaataaaaa ttatctataa tctcagaacc cagaaatagc cactattaac atttcctacg      4680 tatttattt  tacatagatc atattgtata tagttagtat ctttattaat ttttattatg      4740
aaactttcct ttgtcattat tagtcttcaa aagcatgatt tttaatagtt gttgagtatt      4800
ccaccacagg aatgtatcac aacttaaccg ttcccgtttg ttagactagt ttcttattaa      4860
tgttgatgaa tgttgtttaa aaataatttt gttgctacat ttactttaat ttccttgact      4920
gtaaagagaa gtaattttgc tccttgataa agtattatat taataataaa tctgcctgca      4980 acttttttgcc ttctttcata atc                                             5003

<210> SEQ ID NO 3
<211> LENGTH: 3214
<212> TYPE: DNA
<213> ORGANISM: Unknown
<220> FEATURE:
<223> OTHER INFORMATION: Plasmid vector

<400> SEQUENCE: 3
ttttgtaata cgactcacta tagggcggcc gggaattcgt cgactggatc cggtaccgag       60
gagatctgcc gccgcgatcg ccatgcccgc cagcgccccg ccgcgccgcc gcggccgcc       120 gccgccgtcg ctgtcgctgc tgctggtgct gctgggcctg gcggccgcc  gcctgcgtgc      180 ggagccgggc gacggcgcgc agacctgggc ccgtttctcg cggcctcctg cccccgaggc      240
cgcgggcctc ttccagggca ccttccccga cggcttcctc tgggccgtgg gcagcgccgc      300
ctaccagacc gagggcggct ggcagcagca cggcaagggt gcgtccatct gggatacgtt      360
cacccaccac cccctggcac cccgggaga ctcccggaac gccagtctgc cgttgggcgc       420
cccgtcgccg ctgcagcccg ccaccgggga cgtagccagc gacagctaca acaacgtctt      480
ccgcgacacg gaggcgctgc gcgagctcgg ggtcactcac taccgcttct ccatctcgtg      540
ggcgcgagtg ctccccaatg gcagcgcggg cgtccccaac cgcgagggc tgcgctacta      600 ccggcgcctg ctggagcggc tgcgggagct gggcgtgcag cccgtggtca ccctgtacca      660
ctgggacctg cccagcgcc tgcaggacgc ctacggcggc tgggccaacc gcgccctggc      720
cgaccacttc agggattacg cggagctctg cttccgccac ttcggcggtc aggtcaagta      780
ctggatcacc atcgacaacc cctacgtggt ggcctggcac ggctacgcca ccgggcgcct      840
ggcccccggc atcggggca gccgcgcct cgggtacctg gtggcgcaca acctcctcct      900
ggctcatgcc aaagtctggc atctctacaa tacttctttc cgtcccactc agggaggtca      960
ggtgtccatt gccctaagct ctcactggat caatcctcga agaatgaccg accacagcat      1020
caaagaatgt caaaaatctc tggactttgt actaggttgg tttgccaaac ccgtattttat      1080 tgatggtgac tatcccgaga gcatgaagaa taacctttca tctattctgc ctgattttac      1140
tgaatctgag aaaaagttca tcaaaggaac tgctgacttt tttgctcttt gctttggacc      1200
caccttgagt tttcaacttt tggaccctca catgaagttc gccaattgg aatctcccaa      1260 cctgaggcaa ctgctttcct ggattgacct tgaatttaac catcctcaaa tatttattgt      1320
ggaaaatggc tggtttgtct cagggaccac caagagagat gatgccaaat atatgtatta      1380
cctcaaaaag ttcatcatgg aaaccttaaa agccatcaag ctggatgggg tggatgtcat      1440
cgggtatacc gcatggtccc tcatggatgg tttcgagtgg cacagaggtt acagcatcag      1500
```

-continued

```
gcgtggactc ttctatgttg actttctaag ccaggacaag atgttgttgc caaagtcttc    1560
agccttgttc taccaaaagc tgatagagaa aaatggcttc cctcctttac ctgaaaatca    1620
gcccctagaa gggacatttc cctgtgactt tgcttgggga gttgttgaca actacattca    1680
agtagatacc actctgtctc agtttaccga cctgaatgtt tacctgtggg atgtccacca    1740
cagtaaaagg cttattaaag tggatggggt tgtgaccaag aagaggaaat cctactgtgt    1800
tgactttgct gccatccagc cccagatcgc tttactccag gaaatgcacg ttacacattt    1860
tcgcttctcc ctggactggg ccctgattct ccctctgggt aaccagtccc aggtgaacca    1920
caccatcctg cagtactatc gctgcatggc cagcgagctt gtccgtgtca acatcacccc    1980
agtggtggcc ctgtggcagc ctatggcccc gaaccaagga ctgccgcgcc tcctggccag    2040
gcagggcgcc tgggagaacc cctacactgc cctggccttt gcagagtatg cccgactgtg    2100
cttccaagag ctcggccatc acgtcaagct ttggataacg atgaatgagc cgtatacaag    2160
gaatatgaca tacagtgctg gccacaacct tctgaaggcc catgccctgg cttggcatgt    2220
gtacaatgaa aagtttaggc atgctcagaa tgggaaaata tccatagcct tgcaggctga    2280
ttggatagaa cctgcctgcc ctttctccca aaaggacaaa gaggtggccg agagagtttt    2340
ggaatttgac attggctggc tggctgagcc catttttcggc tctggagatt atccatgggt    2400
gatgagggac tggctgaacc aaagaaacaa ttttcttctt ccttatttca ctgaagatga    2460
aaaaaagcta atccagggta cctttgactt tttggcttta agccattata ccaccatcct    2520
tgtagactca gaaaaagaag atccaataaa atacaatgat tacctagaag tgcaagaaat    2580
gaccgacatc acgtggctca actcccccag tcaggtggcg gtagtgccct gggggttgcg    2640
caaagtgctg aactggctga agttcaagta cggagacctc cccatgtaca taatatccaa    2700
cggaatcgat gacgggctgc atgctgagga cgaccagctg agggtgtatt atatgcagaa    2760
ttacataaac gaagctctca agcccacat actggatggt atcaatcttt gcggatactt    2820
tgcttattcg tttaacgacc gcacagctcc gaggtttggc ctctatcgtt atgctgcaga    2880
tcagtttgag cccaaggcat ccatgaaaca ttacaggaaa attattgaca gcaatggttt    2940
cccgggccca gaaactctgg aaagattttg tccagaagaa ttcaccgtgt gtactgagtg    3000 cagtttttt cacacccgaa agtctttact ggctttcata gctttctat tttttgcttc     3060 tattatttct ctctccctta tatttacta ctcgaagaaa ggcagaagaa gttacaaaac    3120
gcgtacgcgg ccgctcgagc agaaactcat ctcagaagag gatctggcag caaatgatat    3180
cctggattac aaggatgacg acgataaggt ttaa                                3214
```

PROCESS TO PRODUCE KLOTHO PROTEIN IN VITRO

CROSS-REFERENCE TO RELATED APPLICATION

This application claims the benefit of priority of U.S. provisional application No. 62/705,083, filed Jun. 10, 2020, the contents of which are herein incorporated by reference.

BACKGROUND OF THE INVENTION

The present invention relates to the field of improving the condition and the appearance of aging skin and, more particularly, to a method of producing an aging suppression protein in vitro.

Aging is a multifactorial process where the imbalance between free radical production and antioxidant capacity plays a critical role. Aged skin is characterized by a reduction in cell regeneration in the epidermis and a drop in the production of collagen structural proteins in the dermis. The skin becomes less elastic and its water content is reduced. Aging of the skin is not just a problem cosmetically. Aged skin is accompanied by reduced barrier function and thus diminished protection from environmental exposure. This prompts a fatal progression, accelerating aging of the skin even more.

The skin, our largest organ, provides our barrier to the external world and is the first organ to trigger our immune response. Fibroblasts, otherwise known as skin cells, are one of the first cells to respond to wound healing by secreting communication signals termed growth factors (GFs) to signal cellular proliferation and repair. As we age, the body produces less fibroblast cells and less growth factors which inhibits the body's ability to defend itself against ultraviolet (UV) radiation and harmful environmental factors. Exposure to extreme environments of high temperatures, stress, poor nutrition, and lack of sleep cause free-radical damage and increased oxidative stress in cells.

The Klotho gene encodes a 130-kDa single-pass type I transmembrane protein (Klotho) that forms a complex with multiple fibroblast growth factor (FGF) receptors and functions as an obligatory co-receptor for fibroblast growth factor-23 (FGF23) and has a similar sequence to a beta glycoside enzyme. Klotho is an evolutionarily highly conserved protein related to aging suppression and organ protection. Klotho is the first documented aging suppressor gene in mammals. Klotho was originally identified in 1997 in the kidney (in cortical renal tubules) and was then found to be expressed in other tissues such as blood vessels, placenta, small intestine, and prostate. Klotho is downregulated in chronic kidney disease and/or renal failure, renal cell carcinomas, hepatocellular carcinomas, ataxia, diabetes, and skin atrophy. Klotho-deficient mice exhibit a variety of phenotypes resembling human premature-aging syndromes (including shortened lifespan, growth retardation, infertility, skin atrophy, muscle wasting, hypoglycemia, vascular calcification in the kidneys, osteoporosis, arteriosclerosis, and pulmonary emphysema) (Kuro-o, 2009, Biochim. Biophys. Acta. 1790(10):1049-1058). Klotho deficient mice have increased serum levels of phosphate, unveiling a potential link between phosphate metabolism and aging.

A novel bone-kidney endocrine axis mediated by FGF23 and Klotho has been proposed as the primary mechanism for endocrine regulation of phosphate and vitamin D metabolism. Of note, high vitamin D by itself can trigger apoptosis and potentially cause tissue atrophy. Because serum levels of active vitamin D are greatly increased upon genetic ablation of FGF23 or Klotho, these molecules appear to have a dual role in suppression of apoptotic actions of vitamin D through both negative regulation of 1α-hydroxylase expression and phosphoinositide-3 kinase-dependent inhibition of caspase activity. Notably, it has been demonstrated that signal transduction pathways initiated by FGF23-Klotho prevent tissue atrophy by stimulating proliferation and preventing apoptosis caused by excessive systemic vitamin D. (Medici, et al., 2008, J. Cell Biol. 182(3):459-465).

Upregulation of the Klotho gene increases DNA repair and detoxification of reactive oxygen species. Overexpression of the Klotho gene extends the lifespan and increases resistance to oxidative stress relative to wild-type mice, even without restricted calorie intake (Kurosu et al., Science 309:1829-1833 (2005); Yamamoto et al., J. Biol. Chem. 280:38029-38034 (2005)).

Taken together, these observations suggest that the Klotho gene is an aging-suppressor gene identified in mammals that extends life span when over-expressed and causes a premature-aging syndrome when disrupted. Without being bound by theory, Klotho is believed to function as an aging suppressor system via a common signal transduction pathway. (Kurosu, et al., 2006, J. Biol. Chem. 281:6120-6123; Urakawa, et al., 2006, Nature 444:770-774).

The Klotho protein is reported to mediate its longevity effects by inhibiting the insulin/IGF-1 signaling. Suppression of this signaling pathway is regarded as a central mechanism in the calorie restriction-induced longevity phenomenon. Without being bound by theory, the dietary regimen of Calorie restriction (CR) is believed to be an anti-aging strategy, and it has been reported that, at the cellular level, CR activates detoxification of reactive oxygen species and increases DNA repair. CR causes a decrease in the nutrient (glucose and insulin) levels and adenosine triphosphate (ATP), which leads to a downregulation of the insulin/Insulin-like growth factor-1 (IGF-1) signaling pathway (which serves as a cellular sensor for nutrients) and an upregulation of the adenosine monophosphate (AMP)-activated protein kinase (AMPK).

The AMPK is a cellular sensor for energy which is activated by an increased AMP/ATP ratio indicating low energy. During calorie restriction and after exercise, AMPK activity is increased to restore the ATP level by stimulating ATP-generating processes and by inhibiting ATP-consuming processes that are not needed for survival. But the role of AMPK is not restricted to the control of the energy metabolism. AMPK is a type of master switch that was shown to regulate several transcription factors related to longevity and aging. AMPK can activate the forkhead box (FOX) transcription factor FOXO and the transcription factor Nuclear factor erythroid-2-related factor 2 (Nrf2), that control the response to different types of stress, regulating the cell cycle and promoting cell survival via DNA damage repair and free radical detoxification in the cells. Normally, under high nutrient and insulin conditions, the receptor gets phosphorylated, leading to inactivation of the transcription factor FOXO inside the cell. Under low-nutrient conditions, this signaling pathway is blocked. AMPK blocks NF-κB and thus inhibits inflammatory reactions. Stimulation of AMPK activity induces anti-aging effects and confers longevity. (Mibelle® Biochemistry marketing materials, "Snow Algae Powder. Key to skin's longevity"). Therefore, Klotho has been proposed to induce a calorie-restriction-like anti-aging response.

Increased expression of the Klotho gene leads to an increase in antioxidant enzymes such as Sodium Oxide Dismutase (SOD2) and Catalase. There is growing evidence that Klotho increases nitric oxide bioavailability through the induction of mitochondrial superoxide dismutase (MnSOD) and suppression of nicotinamide adenine dinucleotide phosphate (NADPH) oxidases protecting against oxidative stress and reactive oxygen species (ROS). More recently, the idea of implementing the use of growth factors in topical anti-aging has been put into practice. Among such factors include epidermal growth factor (EGF) and fibroblast growth factor basic (FGFb), both of which have been implicated in cellular processes critical to cell proliferation and collagen synthesis. Basic fibroblast growth factor is a membrane-bound growth factor implicated in angiogenesis during wound healing. Other growth factors that have shown a role in wound healing include insulin-like growth factor (IGF), transforming growth factor-$\beta$ (TGFb), and vascular endothelial growth factor (VEGF).

U.S. Pat. No. 6,579,850 describes polypeptides and compositions comprising an $\alpha$-Klotho polypeptide. Human and mouse $\alpha$-Klotho polypeptides are disclosed. The patent also discloses that compositions comprising the polypeptides are useful in treating a syndrome resembling premature aging, treating adult diseases, and suppressing aging.

The human Klotho (KL) gene (National Center for Biotechnology Information [NCBI] Accession number NM004795) encodes a type-I membrane protein that is related to $\beta$-glucosidases. The reduced production of this protein in various mice-genetic models has indicated that this KL gene is involved with skin atrophy, chronic renal failure (CRF), and osteoporosis, and may be one of the factors underlying the degenerative processes seen in CRF.

Accumulating evidence indicates that the anti-aging function of Klotho plays an important role in human aging and age-related diseases. Klotho deficiency is strongly associated with human diseases related to aging such as cancer, chronic kidney disease, ataxia, diabetes, and skin atrophy. Therefore, the Klotho protein we have developed may have other systemic uses.

Klotho is an anti-aging protein with pleiotropic actions that exerts organ protection. Several lines of evidence support the notion that Klotho functions as a human aging-suppression molecule. Polymorphisms of Klotho are correlated with life span, coronary artery disease, atherosclerosis, and osteoporosis in humans. Klotho is also associated with severe calcinosis and stroke. Klotho deficiency is involved in acute and chronic kidney diseases, and salt-sensitive hypertension. The serum level of Klotho decreases with aging in humans. However, the biological function of Klotho and the way in which Klotho deficiency contributes to age-related diseases remain elusive.

The Klotho gene family consists of $\alpha$-, $\beta$- and $\gamma$-Klotho. The $\alpha$-Klotho also plays a role in decreasing aging and improving cognition. Since $\alpha$-Klotho protein does not require cleavage, it may be secreted directly into extracellular space, reaching the blood stream and other body fluids.

The extracellular domain of the Klotho protein is clipped just above the plasma membrane at the cell surface by membrane-anchored proteases A Disintegrin And Metalloprotease (ADAM)10 and ADAM17 to generate a secreted form of Klotho protein which is secreted into the bloodstream, potentially functioning as a humoral/endocrine factor that signals suppression of intracellular insulin/IGF1 signaling, likely playing a role in its anti-aging properties. (Kurosu, et al., 2006, J. Biol. Chem. 281:6120-6123). Interestingly, several aging-like phenotypes are observed in tissues that do not express Klotho endogenously, suggesting that Klotho protein may act as a humoral factor(s). The secreted protein is found in urine, serum, pancreatic juice, and cerebrospinal fluid. Secreted Klotho protein has been reported to protect cells and tissues from oxidative stress. Additionally, the secreted Klotho protein has a putative sialidase activity that modifies glycans on the cell surface, which may explain the ability of secreted Klotho protein to regulate activity of multiple ion channels and growth factors including insulin, IGF-1, and Wnt. Therefore, the transmembrane and clipped/secreted forms of Klotho protein appear to have distinct functions, each of which may affect aging processes in mammals.

The extracellular domain of the $\alpha$-Klotho protein comprises two subdomains, termed KL-D1 and KL-D2. These two subdomains share sequence homology to $\beta$-glucosidase of bacteria and plants. The extracellular domain of the $\alpha$-Klotho protein may be bound to the cell surface by the transmembrane domain or may be cleaved and released into the extracellular milieu. Cleavage of the extracellular domain appears to be facilitated by local low extracellular $Ca^{2+}$ concentrations. $\beta$-Klotho is also a single pass type I transmembrane protein with extracellular KL-D1 and KL-D2 subdomains expressed in adipose tissue, liver, and pancreas. $\beta$-Klotho regulates bile acid metabolism in liver, thus explaining elevated bile synthesis in $\beta$-Klotho deficient mice (Ito et al., J. Clin. Invest. 2005 August; 115(8):2202-8).

Klotho deficiency is also associated with cardiac dysfunction and aging-related augmentation of inflammatory responses. Vascular Klotho deficiency was reported to potentiate the development of human artery calcification and mediate resistance to fibroblast growth factor 23. (Lim K, et al., 2012; Circulation. 125:2243-2255). Recently, post-treatment with recombinant Klotho was found to suppress the inflammatory response and improve cardiac function in aging endotoxemic mice. Klotho modulation of heat shock protein 70 (HSP70) levels appears to be involved in the anti-inflammatory mechanism. HSP70 can modulate the response to inflammatory cytokines such as tumor necrosis factor (TNF)-$\alpha$ and interleukin (IL)-1$\beta$ and may prevent the inflammatory tissue damage caused by aging-related chronic inflammation. (Hui, et al., 2017; Oncotarget 8(9);15663-15676).

PCT Publications WO2017210607 and WO2018098375, assigned to Klotho Therapeutics, Inc., describe recombinant Klotho proteins and variants, nucleic acids encoding them, cell lines, and suspension cultures expressing the same, and a method of manufacturing and administering the same. Proteins include solubility or half-life-extending features like glycosylation and fusion protein tags. Proteins have at least 80% or 85% amino acid sequence identity to a portion of human a Klotho (e.g., isoform 1), and preferably a solubility or half-life extending feature such as glycosylation and/or fusion protein tag. Treatment protocols include determining serum soluble Klotho level in a subject, calculating a dosage of the protein sufficient to raise the serum soluble Klotho level in the subject to a predetermined level, administering the dosage of protein to the subject, such as by bolus or gradual injection, determining a rate of Klotho protein decline in the serum of the subject following administration of the first dosage, calculating a time and amount of a subsequent dosage of the Klotho protein, and administering the subsequent dosage of Klotho protein to the subject.

Various compounds have been tested for treating different types of skin atrophy/aging. Different skin atrophy subtypes respond differently to different anti-aging compositions. At present, although several anti-aging treatments can be employed to reduce the instance of skin atrophy and wrinkles, the results obtained with such therapies are typically poor and those therapies only effect partial reduction in wrinkles at best. No skin care treatment or other process to date has worked with a vector and a promoter to upregulate the Klotho gene in mesenchymal stromal cells (MSC). Nor has any treatment or process isolated the Klotho protein in the cell conditioned medium and then added the Klotho protein to a cosmeceutical composition for skin care. The cosmeceuticals presently available have not been able to utilize the Klotho protein and second-generation growth factors to diminish the visible effects of the aging process on skin.

As can be seen, there is a need for a cosmetic formulation to address the specific needs of aging skin.

A human Klotho protein-expressing MSC cell line has been developed that may produce human Klotho protein-containing condition media. By upregulating the Klotho gene in vitro, collecting the Klotho protein as well as second generation growth factors in the cell conditioned medium, and incorporating the cell conditioned medium into a formulation, a composition may be produced that is believed to address transepidermal water loss (TEWL), skin atrophy due to aging, and free radical damage to the skin due to environmental factors.

SUMMARY OF THE INVENTION

The present invention provides a method of preparing a cell conditioned medium containing growth factors and Klotho protein(s). The present invention provides a method for culturing cells, including providing a cell culture media base, transfecting human fibroblasts, epidermal cells, etc. and allowing the transfected cells to grow, e.g., for at least 24 hours, harvesting the conditioned culture media, removing the cells, and using the conditioned media as an ingredient in a cosmeceutical.

The present invention also provides a conditioned cell culture medium including a cell culture media base and at least one growth factor selected from the group consisting of epidermal growth factor (EGF), fibroblast growth factor basic (FGFb), transforming growth factor beta 1 (TGFβ1), vascular endothelial growth factor (VEGF), insulin-like growth factor (IGF-1), and platelet derived growth factor (PDGF).

A composition may also be provided comprising a conditioned cell culture medium containing combinations of protein components in which the Klotho anti-aging pathway has been activated as human cells are grown in cell culture. The composition may be used in a cosmetic formulation as a topical application applied over time, improving skin cell repair, growth, proliferation, productivity of collagen and/or elastin, reduction of inflammation, and increased hydration to improve the appearance of aging skin. Moreover, an inventive composition comprising the Klotho protein may be administered to patients to improve the condition of multiple organs, including but not limited to the skin, kidney, heart, and the pulmonary system, and the vascular system.

In one aspect of the present invention, a method of producing Klotho protein is provided, comprising preparing a Klotho plasmid DNA vector having a mammalian selection marker and a Klotho open reading frame, culturing cells selected from a group consisting of primary fibroblast cells, mesenchymal stromal cells, and a combination thereof in a cell culture medium, transfecting the cells with the Klotho plasmid DNA vector to produce transfected cells, growing the transfected cells in the cell culture medium to produce a cell culture supernatant containing Klotho protein, and harvesting the cell culture supernatant by removing the transfected cells.

In another aspect of the present invention, a method of manufacturing a cosmetic composition is provided, comprising combining Klotho protein or a cell culture supernatant containing Klotho protein with a cosmetically acceptable vehicle.

In another aspect of the present invention, a method of treating a patient to improve the condition and appearance of aging skin is provided, comprising topically administering an effective amount of a cosmetic composition to the patient, said cosmetic composition comprising Klotho protein or a cell culture supernatant containing Klotho protein and a cosmetically acceptable vehicle.

These and other features, aspects and advantages of the present invention will become better understood with reference to the following drawings, description, and claims.

BRIEF DESCRIPTION OF THE DRAWINGS

FIG. 1 is a full-length amino acid sequence of the human Klotho (α-KL) protein;

Figure 2:
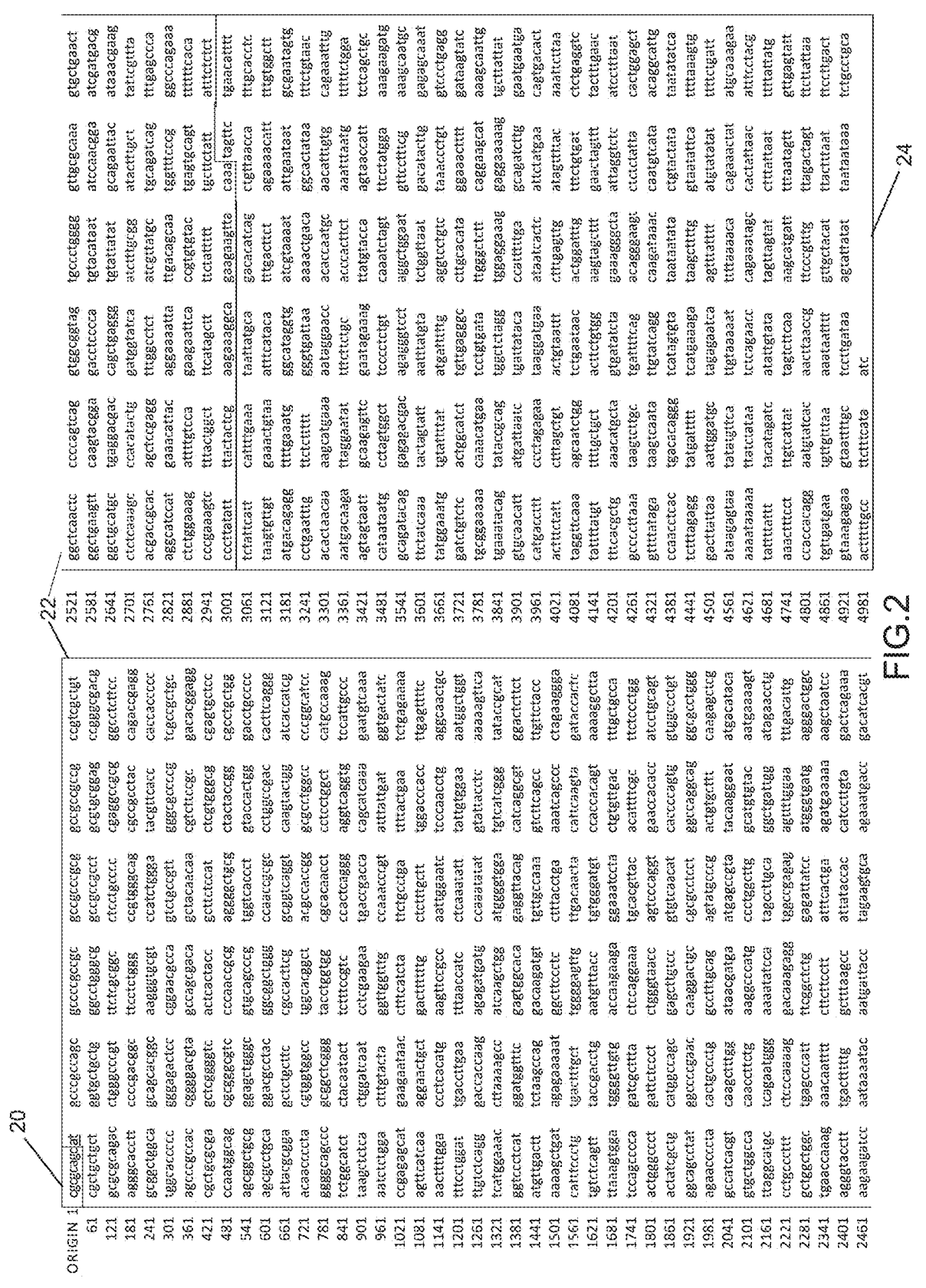

FIG. 2 is a full-length sequence of the human Klotho gene;

FIG. 3 is a coding sequence that may be used to generate α-klotho protein;

FIGS. 8A and 8B are graphs illustrating FBC proliferation cultured in the presence of 8% serum at different cell numbers over time;

DETAILED DESCRIPTION OF THE INVENTION

Figure 4:
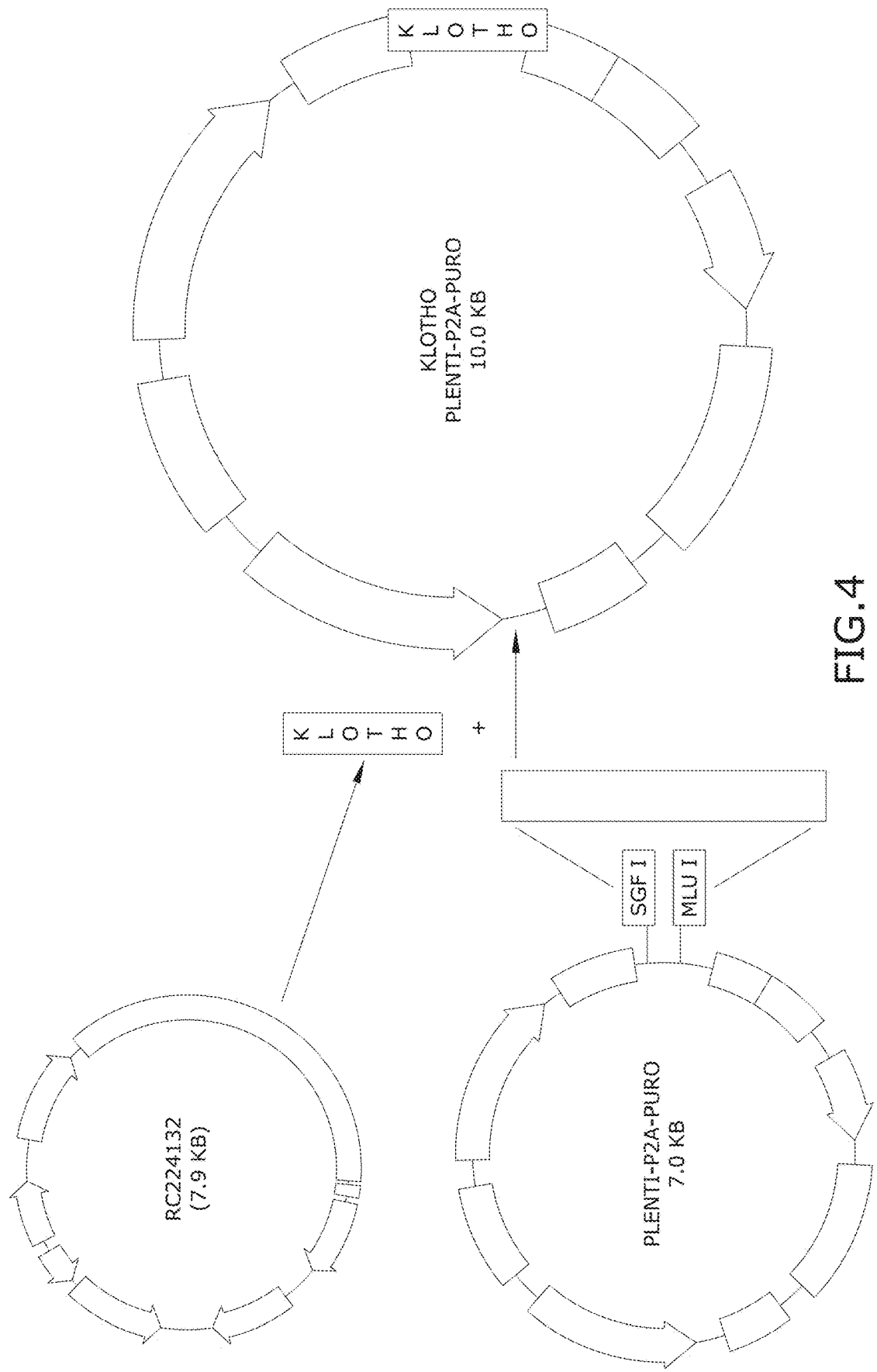
FIG. 4 is a schematic illustrating a method of constructing a klotho plasmid vector from plasmid vector RC224132.

The following detailed description is of the best currently contemplated modes of carrying out exemplary embodiments of the invention. The description is not to be taken in a limiting sense but is made merely for the purpose of illustrating the general principles of the invention, since the scope of the invention is best defined by the appended claims.

Broadly, one embodiment of the present invention is a method for preparing a conditioned cell culture medium, including preparing a Klotho plasmid DNA vector; adding primary fibroblast cells, mesenchymal stromal cells, or a combination thereof to a cell culture medium, transfecting the primary fibroblast cells and/or mesenchymal stromal cells to produce transfected cells, growing the transfected cells in the cell culture medium to produce a conditioned medium, harvesting the conditioned medium, removing the cells, and using the conditioned medium as an ingredient in a cosmeceutical with a cosmetically acceptable vehicle.

The Klotho protein may in some cases be extracted from the conditioned culture media and the extracted Klotho protein may be added to a cosmeceutical composition. In other embodiments, the collected Klotho protein may be combined with other components into a composition suitable for use in other areas in the health field and may be administered as appropriate.

As used in the present disclosure, a cosmetically acceptable vehicle may include but is not limited to a diluent, dispersant or carrier for the active agents to facilitate distribution and uptake when the composition is applied to the skin. Vehicles other than or in addition to water may include liquid or solid emollients, solvents, humectants, thickeners, and powders. A cosmetically acceptable vehicle will usually form from 5% to 99.9%, from 10% to 85%, from 25% to 80%, or from 40% to 70% by weight of the composition, and may, in the absence of other cosmetic adjuncts, form the balance of the composition. The compositions may be in the form of aqueous, aqueous/alcoholic, or oily solutions or elixirs; dispersions of the lotion or serum type; anhydrous or lipophilic gels; emulsions of liquid or semi-liquid consistency, which are obtained by dispersion of a fatty phase in an aqueous phase or conversely by dispersion of an aqueous phase in a fatty phase; suspensions or emulsions of smooth, semi-solid or solid consistency of the cream or gel type; pastes or foams. These compositions are formulated according to the usual techniques as are well known in the art.

The compositions may be in the form of an aqueous serum or gel. These compositions are formulated according to the usual techniques as are well known in the art. The compositions of the invention may further comprise cosmetically useful agents and excipients, e.g. glycerin, cetyl alcohol, capric triglyceride, glyceryl stearate, polyethylene glycol (PEG)-100 stearate, steareth-20, steareth-2, cyclopentasiloxane, phenoxyethanol, lecithin, tocopherol, aloe vera, corn starch, lactose, maltodextrin, dextrose, sucrose, kaolin, mannitol, dicalcium phosphate, sodium chloride, etc. each at a concentration of from about 0.1% to about 10% by weight, usually from about 0.5% to about 5%, and may be present at a concentration of from about 0.5%, 1%, 2%, 3%, 4%, 5%, etc.

Hydrophilic gelling agents include carboxyvinyl polymers (carbomer), acrylic copolymers such as acrylate/alkylacrylate copolymers, polyacrylamides, polysaccharides, such as hydroxypropylcellulose, natural gums and clays, and, as lipophilic gelling agents, representative are the modified clays such as bentones, fatty acid metal salts such as aluminum stearates and hydrophobic silica, or ethylcellulose and polyethylene. Disintegrators, such as croscarmellose, microcrystalline cellulose, corn starch, sodium starch glycolate, and alginic acid may be used in some instances.

Solvents which may be used include the lower alcohols, in particular ethanol and isopropanol, and propylene glycol.

According to certain embodiments of the invention, the composition may comprise from about 0.1% to about 90% by weight of the active component(s), such as from about 1% to about 30% by weight, and may be prepared such that a given volume of the formulation contains a known amount of the active component(s).

The compositions may further comprise components selected from the group consisting of: conditioned culture medium, growth factors, cytokines, a solvent and/or diluent, a chelating agent, a humectant, an activity enhancer, an emulsifier, a moisturizer, an antioxidant, a texturizing agent, a feeling agent, an emollient, a preservative, a structuring agent, a thickening agent, a lubricant, a perfume or fragrance, an astringent, a pigment, a sunscreen, and combinations thereof.

When the compositions of the invention are formulated as an emulsion, the proportion of the fatty phase may range from 5% to 80% by weight, and preferably from 5% to 50% by weight, relative to the total weight of the composition. Oils, emulsifiers, and co-emulsifiers incorporated in the composition in emulsion form are selected from among those used conventionally in the cosmetic or dermatological field. The emulsifier and co emulsifier may be present in the composition at a proportion ranging from 0.3% to 30% by weight, and preferably from 0.5% to 20% by weight, relative to the total weight of the composition.

Emulsifiers which may be used include glyceryl stearate, polysorbate 60, PEG-6/PEG-32/glycol stearate mixture, etc.

An oil or oily material may be present, together with an emollient to provide either a water-in-oil emulsion or an oil-in-water emulsion, depending largely on the average hydrophilic-lipophilic balance (HLB) of the emollient employed. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Exemplary oils which may be used according to this invention include mineral oils (liquid petrolatum), plant oils (liquid fraction of karite butter, sunflower oil), animal oils (perhydrosqualen(e), synthetic oils (purcellin oil), silicone oils (cyclomethicone) and fluoro oils (perfluoropolyethers). Fatty alcohols, fatty acids (stearic acid) and waxes (paraffin wax, carnauba wax and beeswax) may also be used as fats.

Exemplary hydrocarbons which may serve as emollients are those having hydrocarbon chains anywhere from 12 to 30 carbon atoms. Specific examples include mineral oil, petroleum jelly, squalene and isoparaffins.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters may include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Preferred compounds may include cetyl, myristyl, palmitic and stearyl alcohols and acids, for example.

Among the polyols which may serve as emollients are linear and branched chain alkyl polyhydroxyl compounds. For example, propylene glycol, sorbitol and glycerin are generally preferred. Also useful may be polymeric polyols such as polypropylene glycol and polyethylene glycol. Butylene and propylene glycol may be preferred as penetration enhancers.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

The compositions of the invention may also contain additives and adjuvants which are conventional in the cosmetic, pharmaceutical or dermatological field, such as hydrophilic or lipophilic gelling agents, hydrophilic or lipophilic active agents, preservatives, antioxidants, fragrances, fillers, bactericides, odor absorbers and dyestuffs or colorants. The amounts of these various additives and adjuvants are those conventionally used in the field, and, for example, range from 0.01% to 10% of the total weight of the composition. Depending on their nature, these additives and adjuvants may be introduced into the fatty phase or into the aqueous phase.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

Accordingly, a composition of the invention may include additional agents or additives that are not in themselves active agents but play a role in promoting the usefulness or effectiveness of an active agent.

The severity of a subject's wrinkling or skin condition may be rated on a 7-point scale ranging from 1 (very much improved) to 7 (very much worse) as follows:
1=very much improved
2=much improved
3=minimally improved
4=no change
5=minimally worse
6=much worse
7=very much worse Scores in active treatment groups observed to be improved as compared to scores in placebo groups indicate that a composition is effective to improve skin condition and appearance. Two-photon microscopy may be used to image deep in the skin (upper dermis) to help determine effectiveness. As used herein, an effective amount refers to an amount of a cosmetic composition that, when topically applied, improves a patient's skin with a score of at least 3.

The composition administered according to the method of the present invention may be administered topically. Methods of administration may include topical administration, such as intradermal or transdermal dosage forms (transdermal patches, ointments, creams).

The inventive composition may be applied using a dispensing device to deliver a set dose of the composition, such as a metered dosing device, which may, in some embodiments, be adjustable. The dispensing device may be, for example, a syringe.

Dosages may be formulated for once-a-day administration or for multiple daily administrations (e.g., 2, 3 or 4 times a day administration). Alternatively, for convenience, dosage forms may be formulated for less frequent administration (e.g., monthly, bi-weekly, weekly, every fourth day, every third day, or every second day), and formulations which facilitate extended release are known in the art. Preferably, the smallest number of daily applications effective may be used for the particular subject.

Compositions of the invention may be applied to any subject and used to treat a variety of conditions, particularly for the reducing the appearance of fine lines and wrinkles and/or skin atrophy, as well as the appearance of spots and discoloration, reducing the appearance of redness, and brightening skin. A composition of the invention may be formulated as a lotion, which may be applied topically once or more daily.

Referring to FIGS. 1 through 13B, FIG. 1 illustrates the full-length 1,012 amino acid sequence of the human Klotho (α-KL) protein, referred to herein as SEQ ID NO:1. The amino acid sequence includes a signal peptide region 10, an extracellular region 12, a transmembrane region 14, and a cytoplasmic region 16. FIG. 2 shows the full-length 5003 base pair (bp) sequence of the human Klotho gene, referred to herein as SEQ ID NO:2. The sequence includes a coding sequence (CDS) 22 having 3036 bp, flanked by a promoter sequence and a termination sequence 20, 24. The 3036 bp coding sequence 22 is included in FIG. 3 as regions 34, 36. The nucleotide sequence of FIG. 3 is referred to herein as SEQ ID NO:3 and includes a plasmid vector 30, a first cloning site 32, a first unused tag 34, the Klotho open reading frame (ORF) 36, a second cloning site 38, a second unused tag 40, and a second portion of the sequence 42. SEQ ID NO.3 was used in following example to generate α-Klotho protein. First, to generate primary skin cells with Klotho expressing gene, a Klotho containing plasmid vector with mammalian selection marker was constructed with a Klotho open reading frame (ORF).

FIGS. 4-7B illustrate an example of development of a primary skin cell line expressing Klotho protein and collection of the Klotho protein in the conditioned media. The Klotho ORF was excised from plasmid vector RC224132 (Origene™ Rockville, MD, USA; NM_004795 sequence), as shown in FIG. 4, and inserted into the plasmid vector pLenti-P2A-Puro (PS100109; Origene™) at the specific restriction site Sgfl/Mlul. No expression tag sequence, such as mGFP tag or Myc-DDK-tag, was used for the Klotho gene. The correct size and orientation of Klotho ORF insertion in the new vector was confirmed by polymerase chain reaction (PCR). Thus, a new plasmid vector Klotho pLenti-P2A-Puro was developed that may express Klotho protein, is devoid of any expression tag, and may be used for transfection of human primary cells to generate conditioned media containing Klotho protein.

Figure 5:
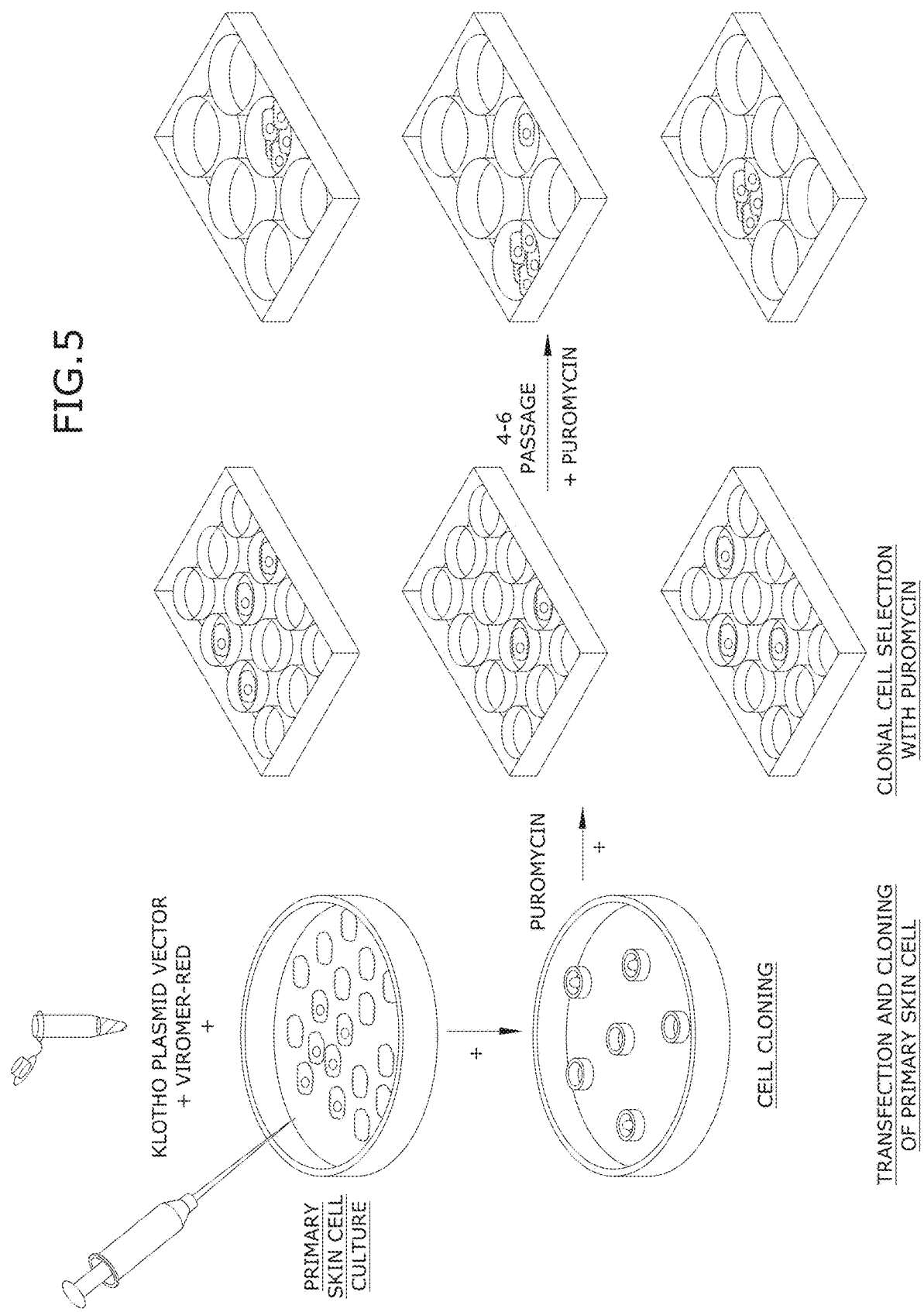
FIG. 5 is a schematic of a method of Klotho cell line generation by transfection of primary fibroblast cells and/or mesenchymal stromal cells with Klotho plasmid DNA vector.

The plasmid vector obtained was used to produce a skin cell line that secretes Klotho protein. Primary fibroblast cells (FBC) and Mesenchymal Stromal cells (MSC) were cultured in Dulbecco's modified Eagle's medium (DMEM)/Medium 199 (M199) (10% fetal bovine serum [FBS]) and DMEM (2% FBS, defined growth factors) respectively, and cultured in a humidified atmosphere of 95% ambient air and 5% $CO_2$ at 37° C. As FIG. 5 illustrates, the skin cells were cultured at 60-70% confluence and then transfected with Klotho plasmid DNA vector pLenti-P2A-Puro in the presence of VIROMER®RED (polyethylenimine polyplex) transfection reagent, under different time periods and conditions. Post 72 hrs. transfection, the cells were treated with Puromycin selective antibiotic (InvivoGen®, USA) at different concentrations. Cells were allowed to grow, viable cells were sub-cultured, and single cell colonies were selected by cloning ring method to produce a skin cell line that expressed and secreted Klotho protein in conditioned media.

Figure 6:
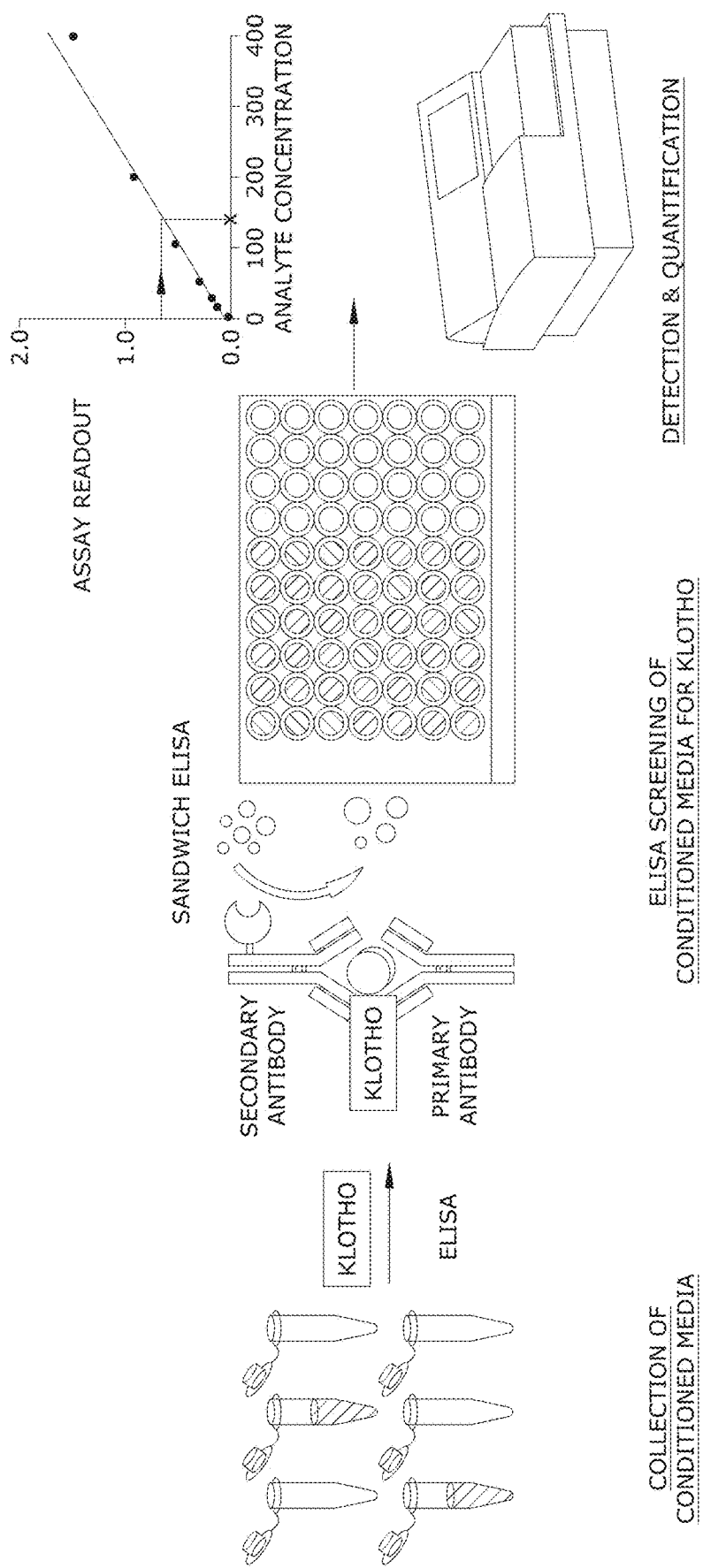
FIG. 6 is a schematic of a method of screening for the Klotho protein using ELISA.
Figure 7A:
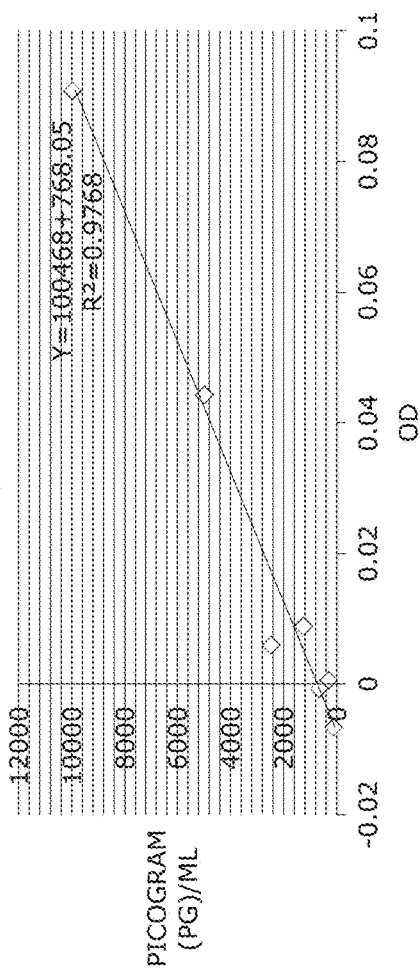
FIG. 7A is a graph illustrating Klotho protein expression detected in conditioned media.
Figure 7B:
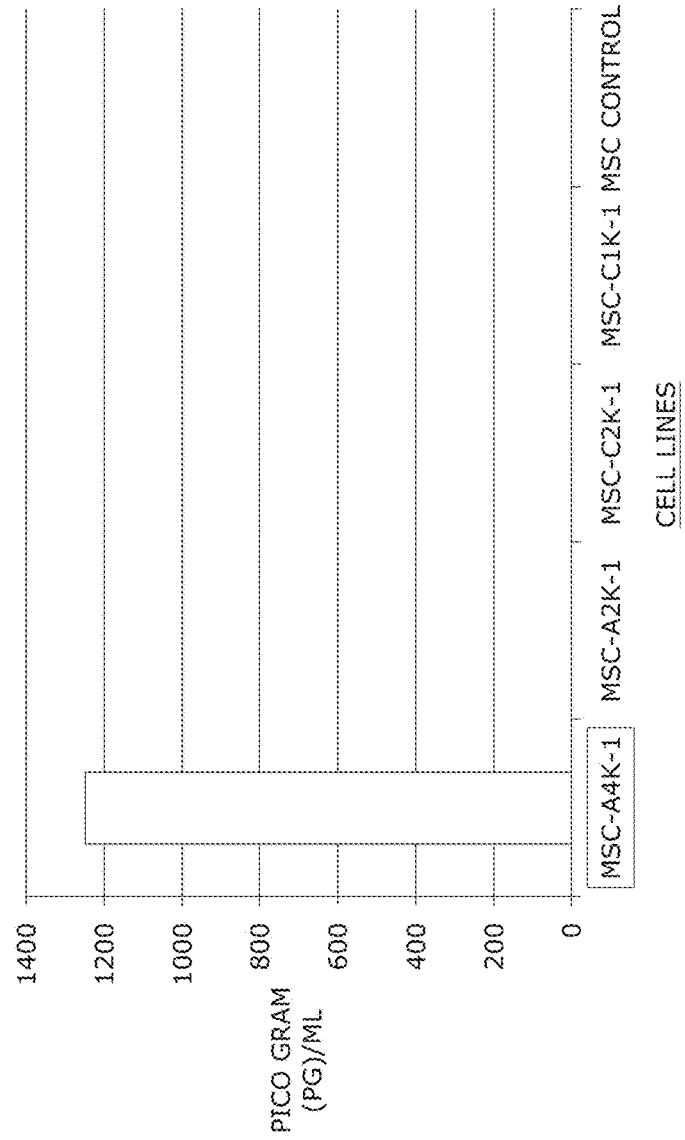
FIG. 7B is a graph showing the standard curve of a positive control.
Figure 9B:
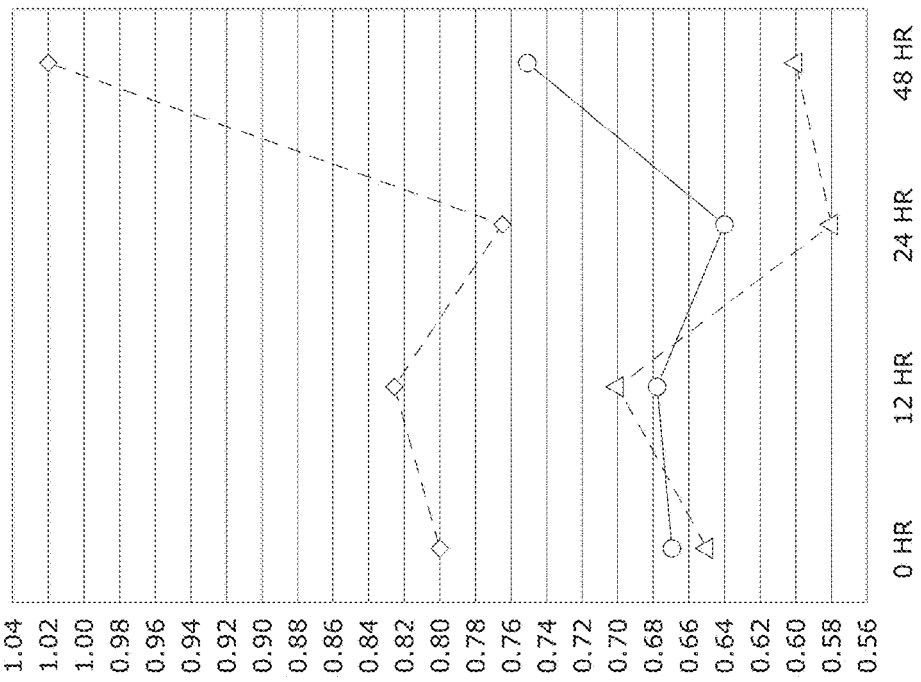
FIGS. 9A and 9B are graphs illustrating FBC proliferation cultured in the presence of 4% serum at different cell numbers over time.
Figure 9A:
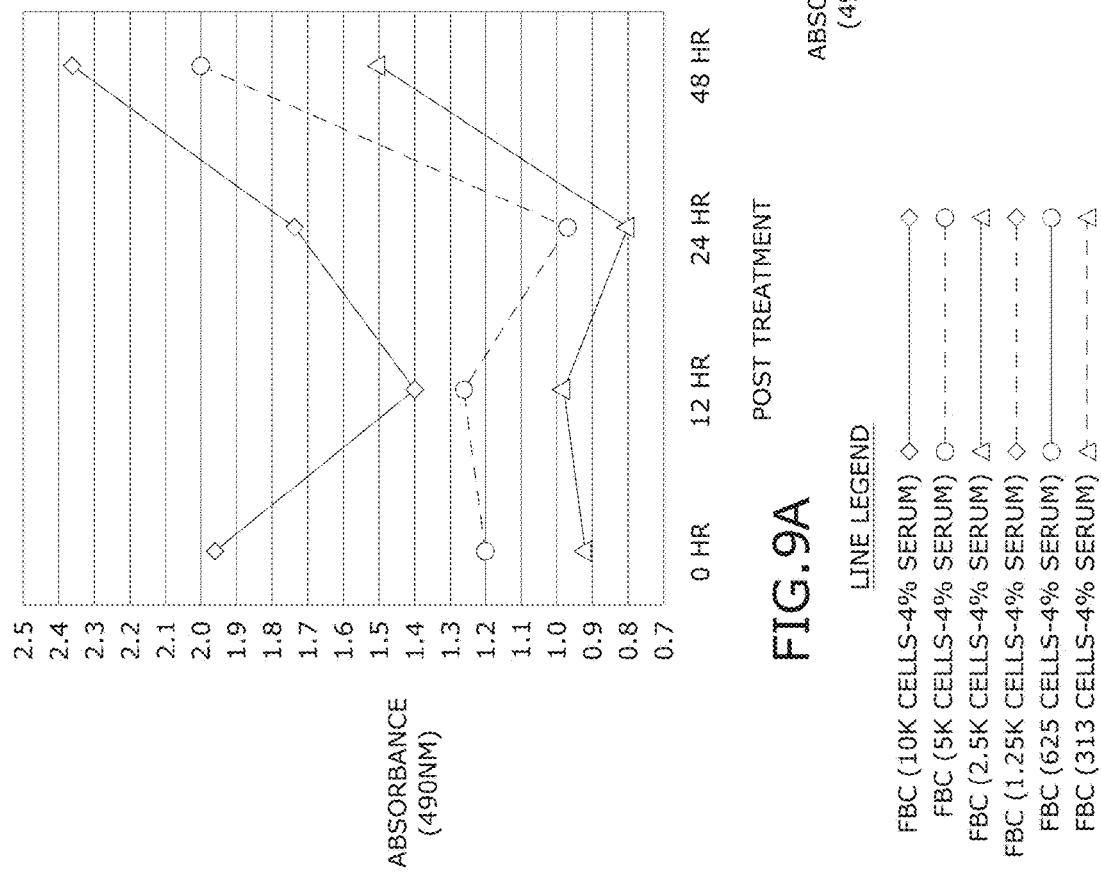
Figure 10B:
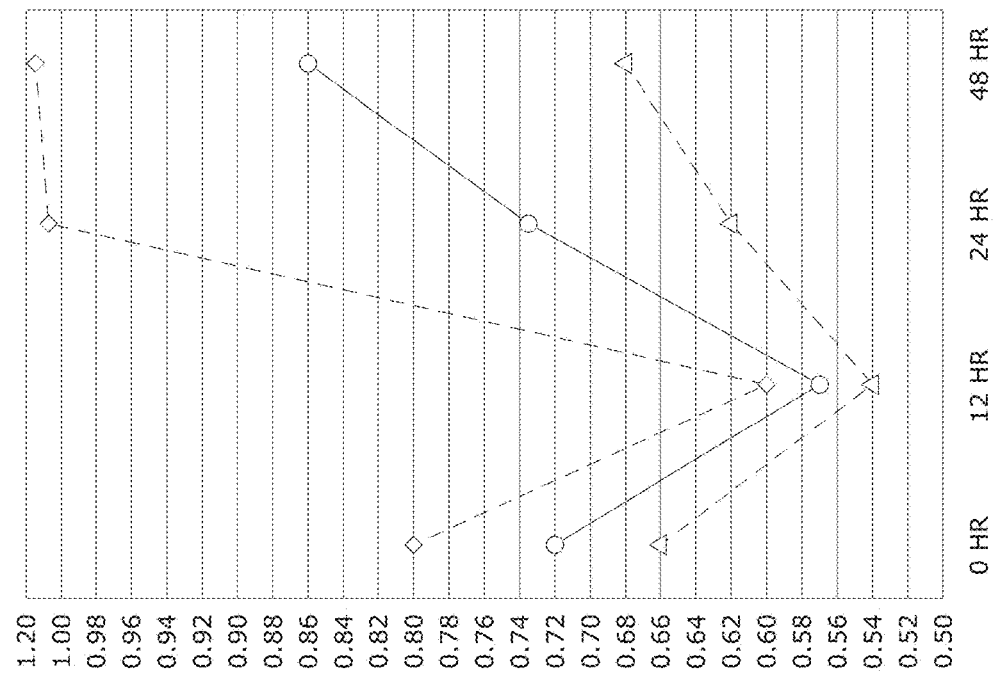
FIGS. 10A and 10B are graphs illustrating FBC proliferation cultured in the presence of 2% serum at different cell numbers over time.
Figure 10A:
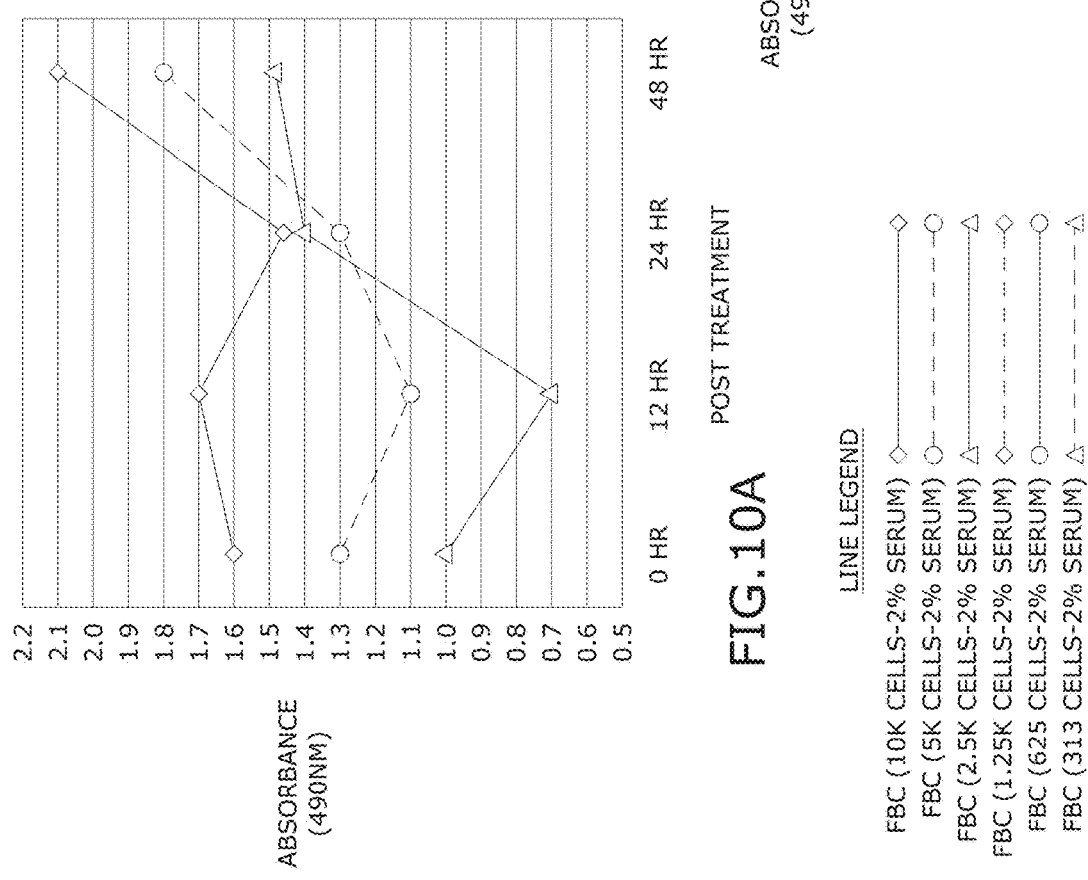
Figure 11B:
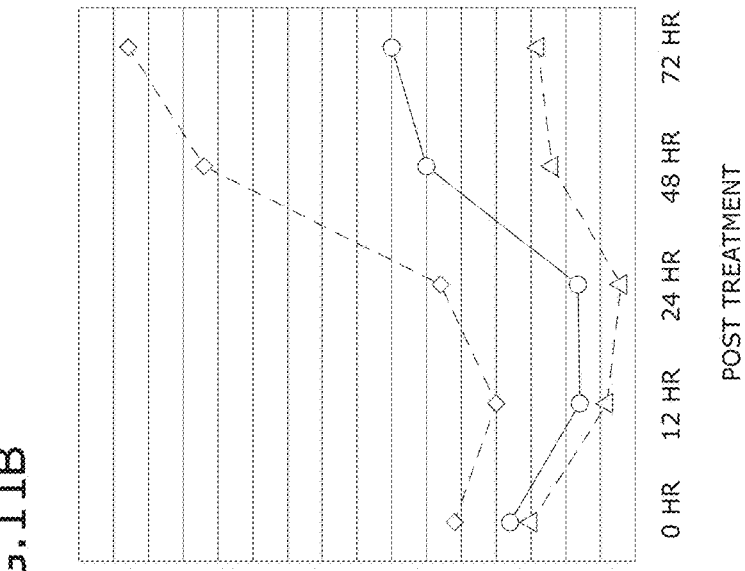
FIGS. 11A and 11B are graphs illustrating MSC proliferation cultured in the presence of 2% serum at different cell numbers over time.
Figure 11A:
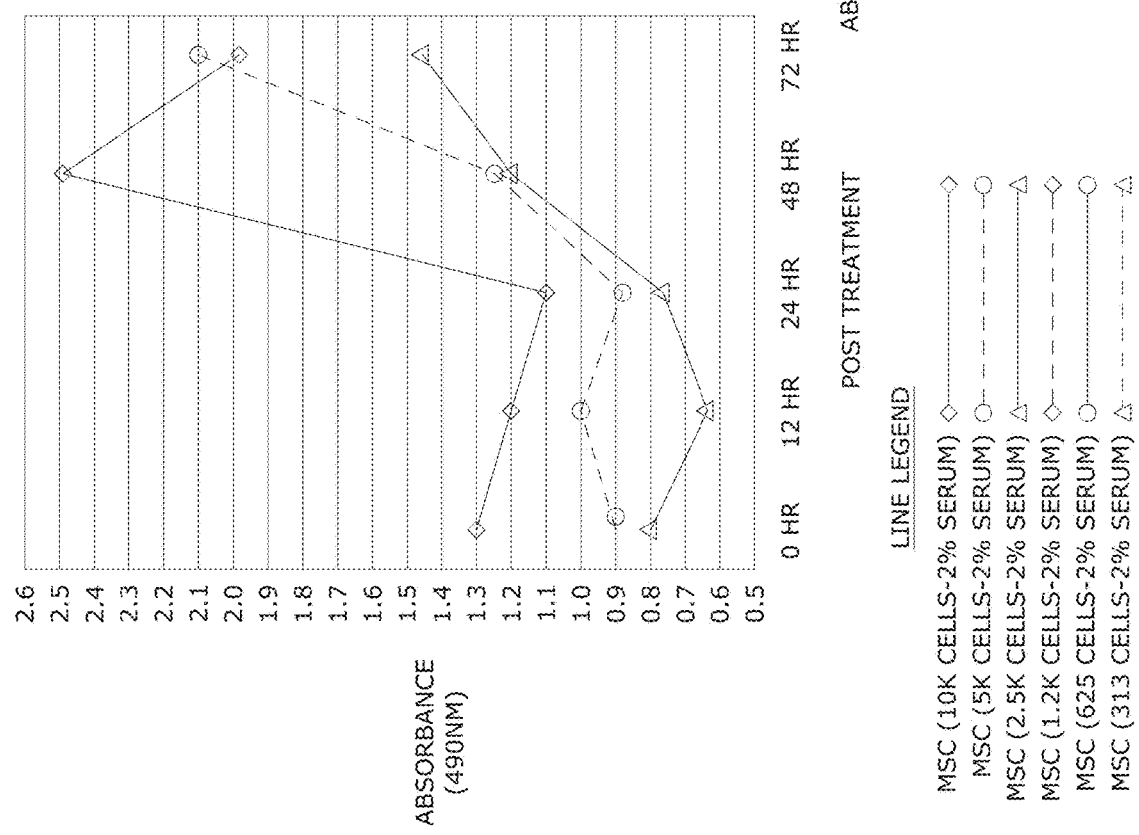
Figure 13A:
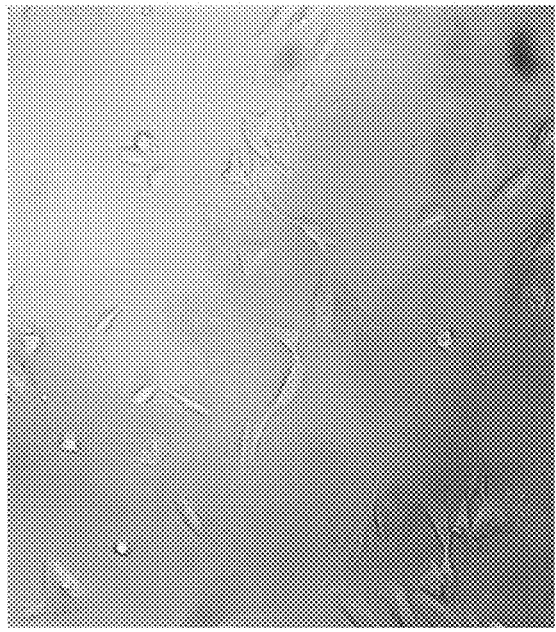
FIGS. 13A and 13B are microphotographs of cultured MSC cells at 40× (FIG. 13A) and 100× (FIG. 13B) magnification.
Figure 13B:
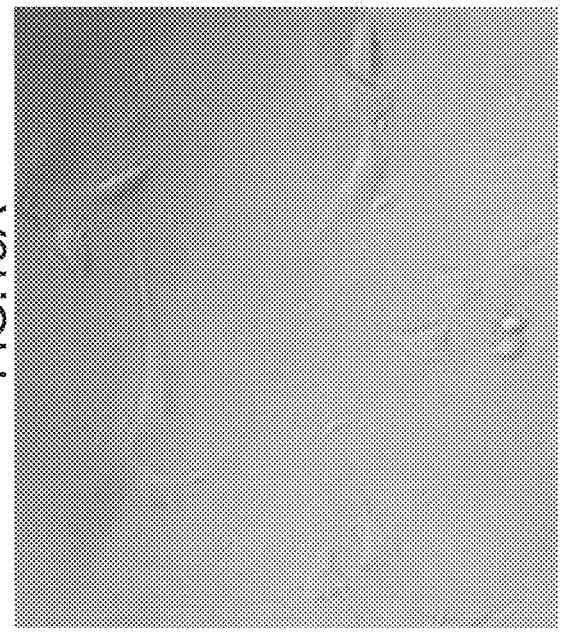
Figure 12A:
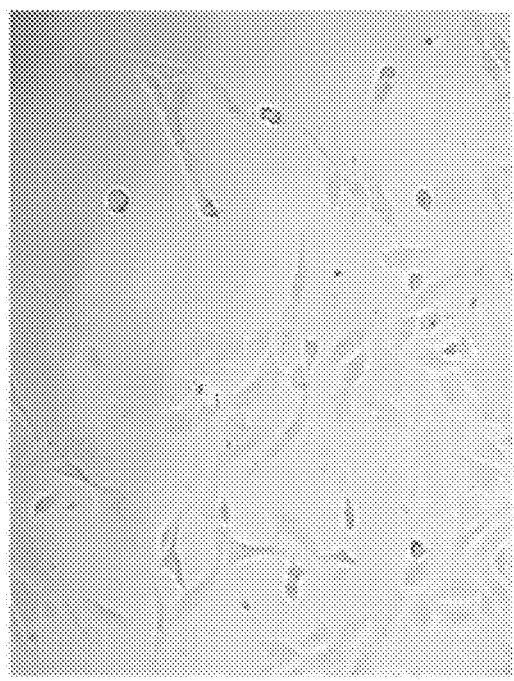
FIGS. 12A and 12B are microphotographs of cultured FBC cells at 40× (FIG. 12A) and 100× (FIG. 12B) magnification.
Figure 12B:

Each single cell colony was maintained separately in Puromycin containing selection media. Stable colonies were generated by selection in complete media containing 0.5-1 µg/ml of Puromycin. The cell culture supernatant (i.e., conditioned media) was collected after 4-6 sub-culture iterations for the detection and quantification of Klotho protein using an enzyme-linked immunoassay (ELISA) Kit (EA102490; ORIGENE) as shown in FIG. 6. The results are shown in FIG. 7A. Of the several conditioned media tested from FBC and MSC cell lines, the conditioned media from one of the MSC cell lines, MSC-A4K-1, expressed a high level of Klotho protein (1250 pg/ml), as evaluated against a positive control Klotho standard curve shown in FIG. 7B. The parental cell line control (MSC control) and other MSC cell lines did not express any detectable Klotho protein. Conditioned media from Klotho vector transduced FBC cells lines also did not express Klotho protein. Therefore, a human Klotho protein-expressing MSC cell line was developed that may produce human Klotho protein-containing conditioned media.

FIGS. 8A-13B illustrate another example. FIGS. 8A-10B are graphs of the growth pattern of FBC cultured in the presence of 8%, 4%, and 2% of Fetal Bovine Serum (hereinafter "serum"). FIGS. 11A and 11B are graphs of the growth pattern of MSC grown in defined growth media containing 2% serum. The cells were incubated in a humidified tissue culture incubator at 37° C. in the presence of 5% carbon dioxide ($CO_2$). The cells were allowed to settle and adhere to the bottom of the plate overnight (10-12 hours). The next day, the cells were washed twice with serum-free media and allowed to incubate in serum-free conditions for 12 hours (i.e., serum starved). The serum-containing media was then added. To determine the number of viable cells (i.e., cell proliferation/growth assay), the Cell Titer 96 $Aq_{ueous}$ One Solution Cell Proliferation assay reagent from Promega, USA was used. Absorbance at 490 nm was recorded using an ELISA reader. Each culture was evaluated at six different cell numbers, including 10,000, 5,000, 1,250, 625, and 323 cell/well over 96 well cell culture plates, each well having a growth area of 32 cc/well, in 200 µL of growth media, comprising DMEM, Media199, and serum. Cell growth was evaluated at 0 hours, 12 hours, 24 hours, and 48 hours for FBC and at 72 hours for MSC.

FIGS. 12A, 12B, 13A, and 13B are microphotographs of FBC cells and MSC cells, cultured in complete media in a 96 well plate. Each microphotograph was taken with an inverted microscope after 48 hours at 40× (top image) and 100× (bottom image) magnification.

It should be understood, of course, that the foregoing relates to exemplary embodiments of the invention and that modifications may be made without departing from the spirit and scope of the invention as set forth in the following claims.

What is claimed is:

1. A method of producing Klotho protein, comprising:
   a) preparing a Klotho plasmid DNA vector having a mammalian selection marker and a Klotho open reading frame;
   b) culturing human skin mesenchymal stromal cells in a cell culture medium;
   c) transfecting the human skin mesenchymal stromal cells with the Klotho plasmid DNA vector to produce transfected cells;
   d) growing the transfected cells in the cell culture medium to produce a cell culture supernatant containing a secreted Klotho protein; and
   e) harvesting the cell culture supernatant by removing the transfected cells.

2. The method of claim 1, wherein the Klotho plasmid DNA vector is prepared by excising the Klotho open reading frame from a first plasmid vector and inserting the Klotho open reading frame into a second plasmid vector at a predetermined restriction site.

3. The method of claim 2, wherein the second plasmid vector is devoid of an expression tag sequence.

4. The method of claim 2, further comprising analyzing the second plasmid vector by polymerase chain reaction to confirm a predetermined size and orientation.

5. The method of claim 1, wherein the cell culture medium comprises fetal bovine serum and predetermined growth factors.

6. The method of claim 5, wherein the predetermined growth factors are selected from the group consisting of: epidermal growth factor, fibroblast growth factor basic, transforming growth factor beta 1, vascular endothelial growth factor, insulin-like growth factor, platelet derived growth factor, and combinations thereof.

7. The method of claim 1, wherein the human skin mesenchymal stromal cells are incubated in an atmosphere of about 95% ambient air and about 5% $CO_2$ at about 37° C.

8. The method of claim 1, wherein the human skin mesenchymal stromal cells are cultured and transfected at about 60% to about 70% confluence with a transfection reagent.

9. The method of claim 1, wherein the transfected cells are serum starved for about 12 hours after transfecting the human skin mesenchymal stromal cells.

10. The method of claim 1, wherein the transfected cells are treated with an antibiotic about 72 hours after transfection.

11. The method of claim 1, wherein the transfected cells are sub-cultured and single cell colonies are selected by cloning ring method.

12. The method of claim 11, wherein the cell culture supernatant is collected after about 4 to about 6 sub-culture iterations.

13. A method of manufacturing a cosmetic composition, comprising the method of claim 1 and further combining the harvested cell culture supernatant containing the secreted Klotho protein with a cosmetically acceptable vehicle, an emollient, and a hydrophilic gelling agent.

14. A method of treating a patient to improve aging skin condition and appearance, comprising the method of claim 13 and further topically administering an effective amount of the cosmetic composition to the patient.

15. The method of claim 1, wherein the steps of culturing and transfecting further comprise human primary fibroblast cells together with the human skin mesenchymal stromal cells.

16. The method of claim 1, wherein the Klotho plasmid DNA vector has a sequence comprising SEQ ID NO: 3.

* * * * *